United States Patent
Emborg et al.

(10) Patent No.: US 12,147,357 B2
(45) Date of Patent: Nov. 19, 2024

(54) PERSONAL CARE SYSTEM WITH MONITOR DEVICE AND RELATED METHODS

(71) Applicant: Coloplast A/S, Humlebaek (DK)

(72) Inventors: Jonas Emborg, Frederikssund (DK); Jais Ask Hansen, Jaegerspris (DK); Finn Speiermann, Virum (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 17/918,622

(22) PCT Filed: Apr. 14, 2021

(86) PCT No.: PCT/DK2021/050105
§ 371 (c)(1),
(2) Date: Oct. 13, 2022

(87) PCT Pub. No.: WO2021/209105
PCT Pub. Date: Oct. 21, 2021

(65) Prior Publication Data
US 2023/0141719 A1 May 11, 2023

(30) Foreign Application Priority Data
Apr. 14, 2020 (DK) .......................... PA 2020 70225

(51) Int. Cl.
*G06F 13/16* (2006.01)
*A61F 5/44* (2006.01)
(Continued)

(52) U.S. Cl.
CPC ........ *G06F 13/1668* (2013.01); *A61F 5/4404* (2013.01); *A61F 5/445* (2013.01);
(Continued)

(58) Field of Classification Search
CPC ....................................................... H04W 4/80
See application file for complete search history.

(56) References Cited

U.S. PATENT DOCUMENTS 2,327,514 A  8/1943  Fenwick
2,542,233 A  2/1951  Carroll
(Continued)

FOREIGN PATENT DOCUMENTS

CN  103269668 A  8/2013
CN  203786580 U  8/2014
(Continued)

OTHER PUBLICATIONS

Abidoye et al. "Using Wearable Sensors for Remote Healthcare Monitoring System", Journal of Sensor Technology, 2011, vol. 1, 22-28.

*Primary Examiner* — Henry Tsai
*Assistant Examiner* — Juanito C Borromeo
(74) *Attorney, Agent, or Firm* — Coloplast Corp., Coloplast A/S; Nick Baumann

(57) ABSTRACT

Monitor device of a personal care system, devices of a personal care system and related methods are disclosed. The monitor device comprises a processor; a memory connected to the processor; a first interface connected to the processor, the first interface configured for connecting the monitor device to the personal care appliance; and a second interface comprising a transceiver module connected to the processor and configured for connecting the monitor device to the one or more accessory devices of the personal care system, wherein the monitor device is configured to establish a connection between the monitor device and at least one of the one or more accessory devices; determine whether a primary storing criterion based on a quality of the connection is satisfied; and in accordance with a determination that
(Continued)

the primary storing criterion is satisfied, store primary monitor data in the memory according to a primary storing scheme.

20 Claims, 9 Drawing Sheets

(51) Int. Cl.
    *A61F 5/445*         (2006.01)
    *A61F 13/00*         (2006.01)
    *A61F 13/0206*    (2024.01)
    *G06F 13/42*         (2006.01)

(52) U.S. Cl.
    CPC .... *A61F 13/00051* (2013.01); *A61F 13/0206* (2013.01); *G06F 13/42* (2013.01)

(56) References Cited

U.S. PATENT DOCUMENTS

| | | | |
|---|---|---|---|
| 2,544,579 A | 3/1951 | Ardner |
| 3,214,502 A | 10/1965 | Schaar |
| 3,832,510 A | 8/1974 | Pfau et al. |
| 3,915,171 A | 10/1975 | Shermeta |
| 3,941,133 A | 3/1976 | Chen |
| 4,231,369 A | 11/1980 | Sorensen et al. |
| 4,372,308 A | 2/1983 | Steer et al. |
| 4,449,970 A | 5/1984 | Bevan et al. |
| 4,668,227 A | 5/1987 | Kay |
| 4,754,264 A | 6/1988 | Okada et al. |
| 4,775,374 A | 10/1988 | Cilento et al. |
| 4,834,731 A | 5/1989 | Nowak et al. |
| 4,973,323 A | 11/1990 | Kaczmarek et al. |
| 4,982,742 A | 1/1991 | Claude |
| 5,013,307 A | 5/1991 | Broida |
| 5,016,645 A | 5/1991 | Williams et al. |
| 5,051,259 A | 9/1991 | Olsen et al. |
| 5,074,851 A | 12/1991 | Plass et al. |
| 5,111,812 A | 5/1992 | Swanson et al. |
| 5,237,995 A | 8/1993 | Cano |
| 5,318,543 A | 6/1994 | Ross et al. |
| 5,358,488 A | 10/1994 | Suriyapa |
| 5,486,158 A | 1/1996 | Samuelsen |
| 5,570,082 A | 10/1996 | Mahgerefteh et al. |
| 5,593,397 A | 1/1997 | La Gro |
| 5,626,135 A | 5/1997 | Sanfilippo |
| 5,672,163 A | 9/1997 | Ferreira et al. |
| 5,677,221 A | 10/1997 | Tseng |
| 5,704,905 A | 1/1998 | Jensen et al. |
| 5,790,036 A | 8/1998 | Fisher et al. |
| 5,800,415 A | 9/1998 | Olsen |
| 5,816,252 A | 10/1998 | Faries et al. |
| 5,834,009 A | 11/1998 | Sawers et al. |
| 5,879,292 A | 3/1999 | Sternberg et al. |
| 5,942,186 A | 8/1999 | Sanada et al. |
| 6,015,399 A | 1/2000 | Mracna et al. |
| 6,025,725 A | 2/2000 | Gershenfeld et al. |
| 6,103,033 A | 8/2000 | Say et al. |
| 6,135,986 A | 10/2000 | Leisner et al. |
| 6,171,289 B1 | 1/2001 | Millot et al. |
| 6,206,864 B1 | 3/2001 | Kavanagh et al. |
| 6,407,308 B1 | 6/2002 | Roe et al. |
| 6,433,244 B1 | 8/2002 | Roe et al. |
| 6,482,491 B1 | 11/2002 | Samuelsen et al. |
| 6,485,476 B1 | 11/2002 | Von et al. |
| 6,520,943 B1 | 2/2003 | Wagner |
| 6,677,859 B1 | 1/2004 | Bensen |
| 6,764,474 B2 | 7/2004 | Nielsen et al. |
| 7,066,919 B1 | 6/2006 | Sauerland et al. |
| 7,150,728 B2 | 12/2006 | Hansen et al. |
| 7,166,091 B1 | 1/2007 | Zeltner |
| 7,199,501 B2 | 4/2007 | Pei et al. |
| 7,214,217 B2 | 5/2007 | Pedersen et al. |
| 7,326,190 B2 | 2/2008 | Botten |
| 7,341,578 B2 | 3/2008 | Bulow et al. |
| 7,347,844 B2 | 3/2008 | Cline et al. |
| 7,367,965 B2 | 5/2008 | Poulsen et al. |
| 7,559,922 B2 | 7/2009 | Botten |
| 7,625,362 B2 | 12/2009 | Boehringer et al. |
| 7,641,612 B1 | 1/2010 | McCall |
| 7,670,289 B1 | 3/2010 | McCall |
| 7,943,812 B2 | 5/2011 | Stroebeck et al. |
| 7,981,098 B2 | 7/2011 | Boehringer et al. |
| 8,061,360 B2 | 11/2011 | Locke et al. |
| 8,277,427 B2 | 10/2012 | Edvardsen et al. |
| 8,319,003 B2 | 11/2012 | Olsen et al. |
| 8,398,575 B1 | 3/2013 | McCall |
| 8,398,603 B2 | 3/2013 | Thirstrup et al. |
| 8,399,732 B2 | 3/2013 | Delund et al. |
| 8,409,158 B2 | 4/2013 | Edvardsen et al. |
| 8,449,471 B2 | 5/2013 | Tran |
| 8,500,718 B2 | 8/2013 | Locke et al. |
| 8,632,492 B2 | 1/2014 | Delegge |
| 8,680,991 B2 | 3/2014 | Tran |
| 8,684,982 B2 | 4/2014 | Nguyen-Demary et al. |
| 8,740,865 B2 | 6/2014 | Krystek et al. |
| 8,795,257 B2 | 8/2014 | Coulthard et al. |
| 8,821,464 B2 | 9/2014 | Hanuka et al. |
| 8,975,465 B2 | 3/2015 | Hong et al. |
| 9,046,085 B2 | 6/2015 | Schoess et al. |
| 9,066,812 B2 | 6/2015 | Edvardsen et al. |
| 9,216,104 B2 | 12/2015 | Thirstrup et al. |
| 9,308,332 B2 | 4/2016 | Heppe |
| 9,322,797 B1 | 4/2016 | Lastinger et al. |
| 9,629,964 B2 | 4/2017 | Wuepper |
| 9,693,908 B2 | 7/2017 | Eriksson et al. |
| 9,770,359 B2 | 9/2017 | Edvardsen et al. |
| 9,788,991 B2 | 10/2017 | Bird |
| 9,867,934 B2 | 1/2018 | Heppe |
| 9,928,341 B2 | 3/2018 | Angelides |
| 10,016,298 B2 | 7/2018 | Thirstrup et al. |
| D826,740 S | 8/2018 | Stevens et al. |
| 10,500,084 B2 | 12/2019 | Hansen et al. |
| 10,531,977 B2 | 1/2020 | Schoess et al. |
| 10,646,370 B2 | 5/2020 | Keleny et al. |
| 10,792,184 B2 | 10/2020 | Hvid et al. |
| 10,799,385 B2 | 10/2020 | Hansen et al. |
| 10,849,781 B2 | 12/2020 | Hansen et al. |
| 10,874,541 B2 | 12/2020 | Seres et al. |
| 10,987,243 B2 | 4/2021 | Thirstrup et al. |
| 11,096,818 B2 | 8/2021 | Thirstrup et al. |
| 11,135,084 B2 | 10/2021 | Seres et al. |
| 11,406,525 B2 | 8/2022 | Seres et al. |
| 11,471,318 B2 | 10/2022 | Hansen et al. |
| 11,612,512 B2 | 3/2023 | Hansen et al. |
| 2002/0019615 A1 | 2/2002 | Roe et al. |
| 2003/0132763 A1 | 7/2003 | Ellenz |
| 2003/0169032 A1 | 9/2003 | Minchole et al. |
| 2004/0006320 A1 | 1/2004 | Buglino et al. |
| 2004/0030305 A1 | 2/2004 | Sakamoto |
| 2004/0036484 A1 | 2/2004 | Tamai |
| 2004/0049145 A1 | 3/2004 | Flick |
| 2004/0078219 A1 | 4/2004 | Kaylor et al. |
| 2004/0100376 A1 | 5/2004 | Lye et al. |
| 2004/0106908 A1 | 6/2004 | Leise et al. |
| 2004/0133175 A1 | 7/2004 | Hagedorn-Olsen |
| 2004/0171999 A1 | 9/2004 | Andersen et al. |
| 2004/0193122 A1 | 9/2004 | Cline et al. |
| 2004/0193123 A1 | 9/2004 | Fenton |
| 2004/0216833 A1 | 11/2004 | Fleming et al. |
| 2005/0054997 A1 | 3/2005 | Buglino et al. |
| 2005/0065488 A1 | 3/2005 | Elliott |
| 2005/0070863 A1 | 3/2005 | Bulow et al. |
| 2005/0085779 A1 | 4/2005 | Poulsen et al. |
| 2005/0101841 A9 | 5/2005 | Kaylor et al. |
| 2005/0240163 A1 | 10/2005 | Andersen |
| 2005/0261645 A1 | 11/2005 | Conrad et al. |
| 2006/0015081 A1 | 1/2006 | Suzuki et al. |
| 2006/0025727 A1 | 2/2006 | Boehringer et al. |
| 2006/0052752 A1 | 3/2006 | McMichael |
| 2006/0194324 A1 | 8/2006 | Faries et al. |
| 2006/0271002 A1 | 11/2006 | Botten |
| 2007/0035405 A1 | 2/2007 | Wada et al. |

(56) References Cited

U.S. PATENT DOCUMENTS

| | | |
|---|---|---|
| 2007/0135782 A1 | 6/2007 | Bager et al. |
| 2007/0185464 A1 | 8/2007 | Fattman et al. |
| 2008/0038536 A1 | 2/2008 | Strobech et al. |
| 2008/0071214 A1 | 3/2008 | Locke et al. |
| 2008/0075934 A1 | 3/2008 | Barlow et al. |
| 2008/0091154 A1 | 4/2008 | Botten |
| 2008/0096726 A1 | 4/2008 | Riley et al. |
| 2008/0140057 A1 | 6/2008 | Wood et al. |
| 2008/0234641 A1 | 9/2008 | Locke et al. |
| 2008/0275327 A1 | 11/2008 | Faarbaek et al. |
| 2008/0278337 A1 | 11/2008 | Huang et al. |
| 2008/0300559 A1 | 12/2008 | Gustafson et al. |
| 2008/0306459 A1 | 12/2008 | Albrectsen |
| 2009/0012501 A1 | 1/2009 | Boehringer et al. |
| 2009/0118687 A1 | 5/2009 | Kristensen et al. |
| 2009/0167286 A1 | 7/2009 | Naylor et al. |
| 2009/0173935 A1 | 7/2009 | Cho et al. |
| 2009/0227969 A1 | 9/2009 | Jaeb et al. |
| 2009/0247970 A1 | 10/2009 | Keleny et al. |
| 2010/0010460 A1 | 1/2010 | Butler |
| 2010/0030167 A1 | 2/2010 | Thirstrup et al. |
| 2010/0072271 A1 | 3/2010 | Thorstensson |
| 2010/0076275 A1 | 3/2010 | Chu et al. |
| 2011/0034890 A1 | 2/2011 | Stroebech et al. |
| 2011/0077497 A1 | 3/2011 | Oster et al. |
| 2011/0130642 A1 | 6/2011 | Jaeb et al. |
| 2011/0246983 A1* | 10/2011 | Brunet ............... G06F 11/1456 709/219 |
| 2012/0013130 A1 | 1/2012 | Jung |
| 2012/0143154 A1 | 6/2012 | Edvardsen et al. |
| 2012/0143155 A1 | 6/2012 | Edvardsen et al. |
| 2012/0258302 A1 | 10/2012 | Hunt et al. |
| 2012/0283678 A1 | 11/2012 | Nguyen-Demary et al. |
| 2013/0018231 A1 | 1/2013 | Hong et al. |
| 2013/0030167 A1 | 1/2013 | Wang et al. |
| 2013/0030397 A1 | 1/2013 | Sabeti |
| 2013/0060213 A1 | 3/2013 | Hanuka et al. |
| 2013/0066285 A1 | 3/2013 | Locke et al. |
| 2013/0072886 A1 | 3/2013 | Schertiger et al. |
| 2013/0086217 A1* | 4/2013 | Price ............... G06F 11/1464 709/217 |
| 2013/0102979 A1 | 4/2013 | Coulthard et al. |
| 2013/0138065 A1 | 5/2013 | Buus |
| 2013/0150769 A1 | 6/2013 | Heppe |
| 2013/0165862 A1 | 6/2013 | Griffith et al. |
| 2013/0192604 A1 | 8/2013 | Persson et al. |
| 2013/0226116 A1 | 8/2013 | Edvardsen et al. |
| 2013/0231620 A1 | 9/2013 | Thirstrup et al. |
| 2013/0254141 A1 | 9/2013 | Barda et al. |
| 2013/0303867 A1 | 11/2013 | Elfstrom et al. |
| 2013/0307570 A1 | 11/2013 | Bosaeus et al. |
| 2013/0324952 A1 | 12/2013 | Krystek et al. |
| 2013/0324955 A1 | 12/2013 | Wong et al. |
| 2014/0051946 A1 | 2/2014 | Arne et al. |
| 2014/0200538 A1 | 7/2014 | Euliano et al. |
| 2014/0236111 A1 | 8/2014 | Casado et al. |
| 2014/0275854 A1 | 9/2014 | Venkatraman et al. |
| 2014/0276501 A1 | 9/2014 | Cisko |
| 2014/0288381 A1 | 9/2014 | Faarbaek et al. |
| 2014/0323909 A1 | 10/2014 | Kim |
| 2014/0327433 A1 | 11/2014 | Anway et al. |
| 2014/0336493 A1 | 11/2014 | Kulach et al. |
| 2015/0231802 A1 | 8/2015 | Quan et al. |
| 2015/0250639 A1 | 9/2015 | Thirstrup et al. |
| 2015/0257923 A1 | 9/2015 | Thirstrup et al. |
| 2015/0342777 A1 | 12/2015 | Seres et al. |
| 2015/0374896 A1 | 12/2015 | Du et al. |
| 2016/0084869 A1 | 3/2016 | Yuen et al. |
| 2016/0158056 A1 | 6/2016 | Davis et al. |
| 2016/0158969 A1 | 6/2016 | McLane et al. |
| 2016/0166438 A1 | 6/2016 | Rovaniemi |
| 2016/0218555 A1 | 7/2016 | Slaby et al. |
| 2016/0235581 A1 | 8/2016 | Keleny et al. |
| 2016/0278990 A1 | 9/2016 | Chen |
| 2016/0305776 A1 | 10/2016 | Mrtensson et al. |
| 2016/0310140 A1 | 10/2016 | Belson et al. |
| 2016/0310329 A1 | 10/2016 | Patel et al. |
| 2016/0361015 A1 | 12/2016 | Wang et al. |
| 2017/0042614 A1 | 2/2017 | Salahieh et al. |
| 2017/0050004 A1 | 2/2017 | Tilson et al. |
| 2017/0055896 A1 | 3/2017 | Al-Ali et al. |
| 2017/0140103 A1 | 5/2017 | Angelides |
| 2017/0156920 A1 | 6/2017 | Hunt et al. |
| 2017/0340474 A1 | 11/2017 | Thirstrup et al. |
| 2017/0348137 A1 | 12/2017 | Hvid et al. |
| 2017/0348162 A1 | 12/2017 | Arizti et al. |
| 2017/0360592 A1 | 12/2017 | Carrubba |
| 2018/0049667 A1 | 2/2018 | Heppe |
| 2018/0055359 A1 | 3/2018 | Shamim et al. |
| 2018/0171183 A1 | 6/2018 | Sakurai et al. |
| 2019/0133810 A1 | 5/2019 | Seres et al. |
| 2019/0133811 A1 | 5/2019 | Seres et al. |
| 2019/0133812 A1 | 5/2019 | Seres et al. |
| 2019/0142623 A1 | 5/2019 | Schoess et al. |
| 2019/0175386 A1 | 6/2019 | Monty |
| 2019/0192066 A1 | 6/2019 | Schoess et al. |
| 2019/0192332 A1 | 6/2019 | Hansen et al. |
| 2019/0192333 A1 | 6/2019 | Hansen et al. |
| 2019/0192334 A1 | 6/2019 | Hansen et al. |
| 2019/0240059 A1 | 8/2019 | Seres et al. |
| 2019/0247050 A1 | 8/2019 | Goldsmith |
| 2019/0374163 A1 | 12/2019 | Faarbaek et al. |
| 2020/0100931 A1 | 4/2020 | Schoess et al. |
| 2020/0188161 A1 | 6/2020 | Seres et al. |
| 2020/0246174 A1 | 8/2020 | Hansen et al. |
| 2020/0246175 A1 | 8/2020 | Hansen et al. |
| 2020/0246176 A1 | 8/2020 | Hansen et al. |
| 2020/0246177 A1 | 8/2020 | Hansen et al. |
| 2020/0276063 A1 | 9/2020 | Alberto |
| 2020/0306074 A1 | 10/2020 | Speiermann et al. |
| 2020/0330258 A1 | 10/2020 | Hansen et al. |
| 2020/0330260 A1 | 10/2020 | Hansen et al. |
| 2020/0337880 A1 | 10/2020 | Hansen et al. |
| 2020/0337881 A1 | 10/2020 | Hansen et al. |
| 2020/0337882 A1 | 10/2020 | Hansen et al. |
| 2020/0337883 A1 | 10/2020 | Hansen et al. |
| 2020/0375499 A1 | 12/2020 | Hansen et al. |
| 2020/0375782 A1 | 12/2020 | Hansen et al. |
| 2020/0375783 A1 | 12/2020 | Hansen et al. |
| 2020/0375784 A1 | 12/2020 | Hansen et al. |
| 2020/0375785 A1 | 12/2020 | Hansen et al. |
| 2020/0375786 A1 | 12/2020 | Hansen et al. |
| 2020/0383637 A1 | 12/2020 | Hansen et al. |
| 2020/0383818 A1 | 12/2020 | Hansen et al. |
| 2020/0383819 A1 | 12/2020 | Sletten et al. |
| 2020/0383820 A1 | 12/2020 | Hansen et al. |
| 2020/0383821 A1 | 12/2020 | Hansen et al. |
| 2020/0390587 A1 | 12/2020 | Svanegaard et al. |
| 2020/0390588 A1 | 12/2020 | Hansen et al. |
| 2020/0390589 A1 | 12/2020 | Hansen et al. |
| 2020/0395120 A1 | 12/2020 | Svanegaard et al. |
| 2020/0395610 A1 | 12/2020 | Ono et al. |
| 2020/0405228 A1 | 12/2020 | Svanegaard et al. |
| 2020/0405229 A1 | 12/2020 | Svanegaard et al. |
| 2020/0405230 A1 | 12/2020 | Svanegaard et al. |
| 2021/0000414 A1 | 1/2021 | Svanegaard et al. |
| 2021/0000633 A1 | 1/2021 | Hansen et al. |
| 2021/0000634 A1 | 1/2021 | Svanegaard et al. |
| 2021/0000635 A1 | 1/2021 | Hansen et al. |
| 2021/0000636 A1 | 1/2021 | Hansen et al. |
| 2021/0007663 A1 | 1/2021 | Svanegaard et al. |
| 2021/0007881 A1 | 1/2021 | Svanegaard et al. |
| 2021/0015653 A1 | 1/2021 | Hansen et al. |
| 2021/0015654 A1 | 1/2021 | Hansen et al. |
| 2021/0022683 A1 | 1/2021 | Faarbaek et al. |
| 2021/0038424 A1 | 2/2021 | Svanegaard et al. |
| 2021/0059603 A1 | 3/2021 | Svanegaard et al. |
| 2021/0085511 A1 | 3/2021 | Hansen et al. |
| 2021/0085512 A1 | 3/2021 | Hansen et al. |
| 2021/0100533 A1 | 4/2021 | Seres et al. |
| 2021/0128364 A1 | 5/2021 | Cole et al. |
| 2021/0177642 A1 | 6/2021 | Andersen et al. |
| 2021/0212855 A1 | 7/2021 | Hansen et al. |
| 2021/0228194 A1 | 7/2021 | Mayberg |

(56) References Cited

U.S. PATENT DOCUMENTS

| | | |
|---|---|---|
| 2021/0338471 A1 | 11/2021 | Nolan et al. |
| 2021/0361464 A1 | 11/2021 | Larsen et al. |
| 2021/0361465 A1 | 11/2021 | Hansen et al. |
| 2021/0361466 A1 | 11/2021 | Hansen et al. |
| 2021/0361467 A1 | 11/2021 | Hansen et al. |
| 2021/0369197 A1 | 12/2021 | Hansen et al. |
| 2021/0369488 A1 | 12/2021 | Hansen et al. |
| 2021/0369489 A1 | 12/2021 | Hansen et al. |
| 2021/0369490 A1 | 12/2021 | Hansen et al. |
| 2021/0386368 A1 | 12/2021 | Carlsson et al. |
| 2022/0000652 A1 | 1/2022 | Thirstrup et al. |
| 2022/0031495 A1 | 2/2022 | Seres et al. |
| 2022/0079802 A1 | 3/2022 | Hansen |
| 2022/0079803 A1 | 3/2022 | Windeballe et al. |
| 2022/0087851 A1 | 3/2022 | Stroebech |
| 2022/0117771 A1 | 4/2022 | Fearn et al. |
| 2022/0142807 A1 | 5/2022 | Tofte |
| 2022/0192860 A1 | 6/2022 | Hansen et al. |
| 2022/0241104 A1 | 8/2022 | Knoedler |
| 2022/0241105 A1 | 8/2022 | Hansen et al. |
| 2022/0265458 A1 | 8/2022 | Carlsson et al. |

FOREIGN PATENT DOCUMENTS

| | | |
|---|---|---|
| CN | 104902399 A | 9/2015 |
| CN | 104980878 A | 10/2015 |
| CN | 105588856 A | 5/2016 |
| CN | 206271160 U | 6/2017 |
| CN | 206450708 U | 8/2017 |
| CN | 107661167 A | 2/2018 |
| DE | 3437950 A1 | 4/1985 |
| DE | 3836590 A1 | 5/1990 |
| DE | 19953062 A1 | 5/2000 |
| DE | 19900611 C1 | 7/2000 |
| DE | 102011014321 A1 | 9/2012 |
| DE | 102011076219 A1 | 11/2012 |
| EP | 0168967 A1 | 1/1986 |
| EP | 0373782 A1 | 6/1990 |
| EP | 0416397 A1 | 3/1991 |
| EP | 0850076 B1 | 4/2005 |
| EP | 1188157 B1 | 12/2005 |
| EP | 2000083 A2 | 12/2008 |
| EP | 2108345 A1 | 10/2009 |
| EP | 2489561 A2 | 8/2012 |
| EP | 2654646 A2 | 10/2013 |
| EP | 3064179 A1 | 9/2016 |
| EP | 3213727 A1 | 9/2017 |
| GB | 2219679 A | 12/1989 |
| GB | 2225951 A | 6/1990 |
| GB | 2343628 A | 5/2000 |
| GB | 2465742 A | 6/2010 |
| GB | 2542093 A | 3/2017 |
| JP | 04-074882 A | 3/1992 |
| JP | 06-152077 A | 5/1994 |
| JP | 09-010184 A | 1/1997 |
| JP | 11-128352 A | 5/1999 |
| JP | 2000-093448 A | 4/2000 |
| JP | 2001-087299 A | 4/2001 |
| JP | 2002-055074 A | 2/2002 |
| JP | 2002-224093 A | 8/2002 |
| JP | 2005-323981 A | 11/2005 |
| JP | 2007-319561 A | 12/2007 |
| JP | 2014-033745 A | 2/2014 |
| JP | 2014-054368 A | 3/2014 |
| JP | 2014-507182 A | 3/2014 |
| KR | 10-2012-0003987 A | 1/2012 |
| NL | 1003904 C2 | 3/1998 |
| RU | 2527155 C2 | 8/2014 |
| TW | 201201783 A | 1/2012 |
| WO | 94/15562 A1 | 7/1994 |
| WO | 97/10012 A1 | 3/1997 |
| WO | 99/33037 A1 | 7/1999 |
| WO | 99/36017 A1 | 7/1999 |
| WO | 00/79497 A1 | 12/2000 |
| WO | 01/13830 A1 | 3/2001 |
| WO | 01/50996 A1 | 7/2001 |
| WO | 02/52302 A2 | 7/2002 |
| WO | 02/99765 A1 | 12/2002 |
| WO | 2005/038693 A1 | 4/2005 |
| WO | 2005/082271 A2 | 9/2005 |
| WO | 2006/008866 A1 | 1/2006 |
| WO | 2006/094513 A2 | 9/2006 |
| WO | 2007/000168 A1 | 1/2007 |
| WO | 2007/059774 A2 | 5/2007 |
| WO | 2007/070266 A1 | 6/2007 |
| WO | 2007/098762 A1 | 9/2007 |
| WO | 2007/133555 A2 | 11/2007 |
| WO | 2008/057884 A2 | 5/2008 |
| WO | 2009/006900 A1 | 1/2009 |
| WO | 2009/052496 A1 | 4/2009 |
| WO | 2009/107011 A1 | 9/2009 |
| WO | 2009/112912 A2 | 9/2009 |
| WO | 2011/003421 A1 | 1/2011 |
| WO | 2011/004165 A1 | 1/2011 |
| WO | 2011/061540 A1 | 5/2011 |
| WO | 2011/105701 A2 | 9/2011 |
| WO | 2011/123018 A1 | 10/2011 |
| WO | 2011/139499 A1 | 11/2011 |
| WO | 2011/161254 A2 | 12/2011 |
| WO | 2012/068386 A1 | 5/2012 |
| WO | 2012/076022 A2 | 6/2012 |
| WO | 2012/084987 A2 | 6/2012 |
| WO | 2013/013197 A1 | 1/2013 |
| WO | 2014/004207 A1 | 1/2014 |
| WO | 2014/086369 A1 | 6/2014 |
| WO | 2015/007284 A1 | 1/2015 |
| WO | 2015/014774 A1 | 2/2015 |
| WO | 2015/084462 A1 | 6/2015 |
| WO | 2015/094064 A1 | 6/2015 |
| WO | 2015/187366 A1 | 12/2015 |
| WO | 2016/132738 A1 | 8/2016 |
| WO | 2016/166731 A1 | 10/2016 |
| WO | 2016/192738 A1 | 12/2016 |
| WO | 2017/023794 A1 | 2/2017 |
| WO | 2017/062042 A1 | 4/2017 |
| WO | 2017/067558 A1 | 4/2017 |
| WO | 2017/067560 A1 | 4/2017 |
| WO | 2017/074505 A1 | 5/2017 |
| WO | 2017/088153 A1 | 6/2017 |
| WO | 2017/136696 A1 | 8/2017 |
| WO | 2017/190752 A1 | 11/2017 |
| WO | 2018/028756 A1 | 2/2018 |
| WO | 2019/094635 A1 | 5/2019 |
| WO | 2019120432 A1 | 6/2019 |
| WO | 2019/161859 A1 | 8/2019 |
| WO | 2019/161860 A1 | 8/2019 |
| WO | 2019/161863 A1 | 8/2019 |
| WO | 2019/174693 A1 | 9/2019 |
| WO | 2019/174695 A1 | 9/2019 |
| WO | 2019/213623 A1 | 11/2019 |
| WO | 2020/035121 A1 | 2/2020 |

\* cited by examiner

PERSONAL CARE SYSTEM WITH MONITOR DEVICE AND RELATED METHODS

The present disclosure relates to a personal care system, devices thereof and related methods. The personal care system comprises a personal care appliance, such as an ostomy appliance or a wound dressing, and a monitor device. In particular, the present disclosure relates to operation of a monitor device and accessory device in scenarios where a connection is lost or degraded, including storing schemes of a monitor device for a personal care appliance.

BRIEF DESCRIPTION OF THE DRAWINGS

The accompanying drawings are included to provide a further understanding of embodiments and are incorporated into and a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
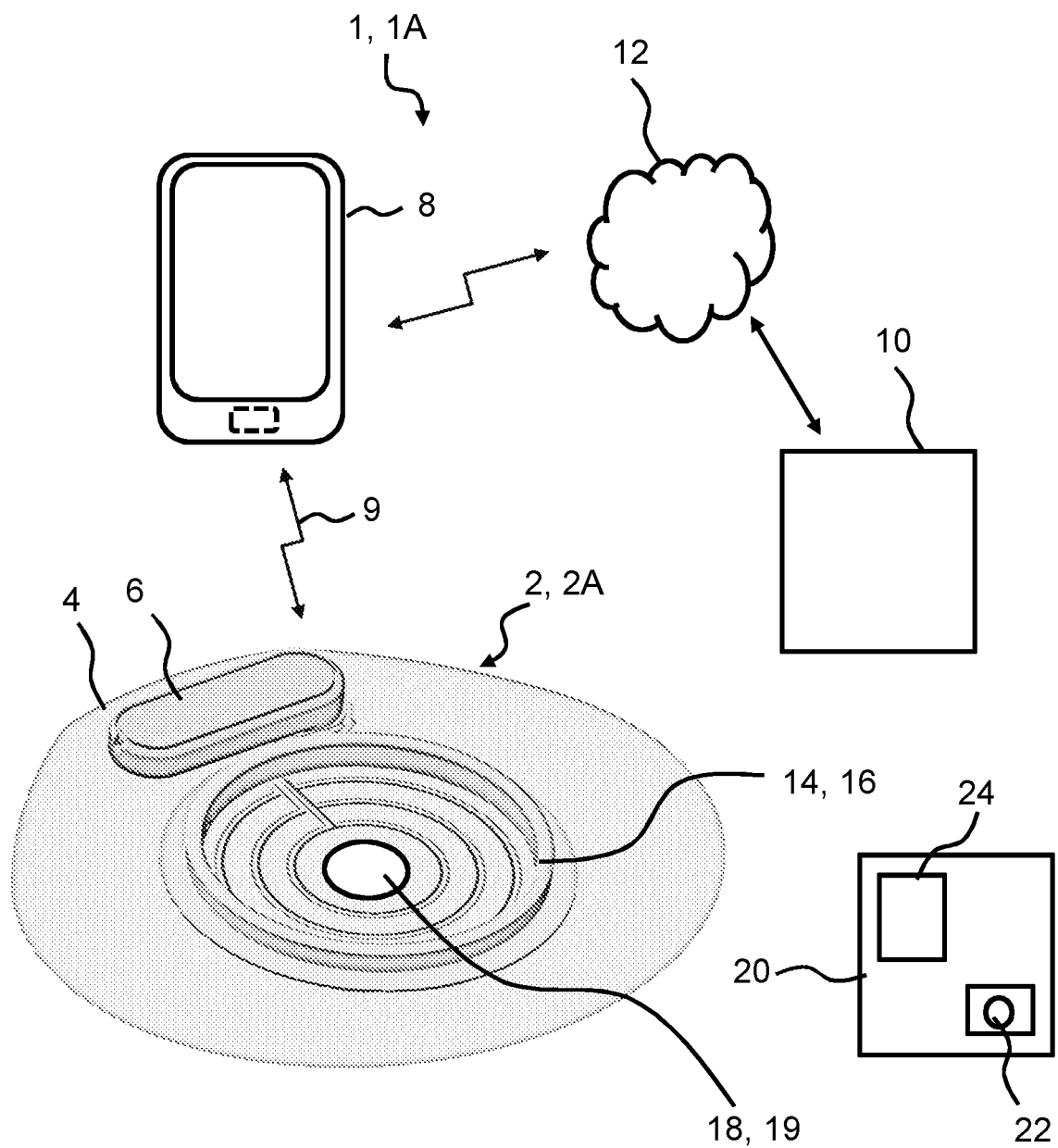
FIG. 1 illustrates an exemplary personal care system being an ostomy system.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout this disclosure, the words "stoma" and "ostomy" are used to denote a surgically created opening bypassing the intestines or urinary tract system of a person. The words are used interchangeably, and no differentiated meaning is intended. The same applies for any words or phrases derived from these, e.g. "stomal", "ostomies" etc.

Also, the solid and liquid wastes emanating from the stoma may be referred to as both stomal "output," "waste(s)," and "fluids" interchangeably. A subject having undergone ostomy surgery may be referred to as "ostomist" or "ostomate"—moreover, also as "patient" or "user". However, in some cases "user" may also relate or refer to a health care professional (HCP), such as a surgeon or an ostomy care nurse or others. In those cases, it will either be explicitly stated, or be implicit from the context that the "user" is not the "patient" him- or herself.

In the following, whenever referring to proximal side or surface of a layer, an element, a device or part of a device, the referral is to the skin-facing side or surface, when a user wears the ostomy appliance. Likewise, whenever referring to the distal side or surface of a layer, an element, a device or part of a device, the referral is to the side or surface facing away from the skin, when a user wears the ostomy appliance/wound dressing appliance. In other words, the proximal side or surface is the side or surface closest to the user, when the appliance is fitted on a user and the distal side is the opposite side or surface—the side or surface furthest away from the user in use.

The axial direction is defined as the direction of the stoma, when a user wears the appliance. Thus, the axial direction is generally perpendicular to the skin or abdominal surface of the user.

The radial direction is defined as perpendicular to the axial direction. In some sentences, the words "inner" and "outer" may be used. These qualifiers should generally be perceived with respect to the radial direction, such that a reference to an "outer" element means that the element is farther away from a centre portion of the ostomy appliance or wound dressing than an element referenced as "inner". In addition, "innermost" should be interpreted as the portion of a component forming a centre of the component and/or being adjacent to the centre of the component. In analogy, "outermost" should be interpreted as a portion of a component forming an outer edge or outer contour of a component and/or being adjacent to that outer edge or outer contour.

The use of the word "substantially" as a qualifier to certain features or effects in this disclosure is intended to simply mean that any deviations are within tolerances that would normally be expected by the skilled person in the relevant field.

The use of the word "generally" as a qualifier to certain features or effects in this disclosure is intended to simply mean—for a structural feature: that a majority or major portion of such feature exhibits the characteristic in question, and—for a functional feature or an effect: that a majority of outcomes involving the characteristic provide the effect, but that exceptionally outcomes do no provide the effect.

The present disclosure relates to a personal care system and devices thereof, such as a personal care appliance, an electrode assembly, a monitor device, and optionally one or more accessory devices, such as a primary accessory device and/or a secondary accessory device. Further, methods related to the personal care system and devices thereof are disclosed. An accessory device (also referred to as an external device), such as the primary accessory device and/or the secondary accessory device, may be a mobile phone or other handheld device, such as a tablet computer. An accessory device, such as the primary accessory device and/or the secondary accessory device, may be a personal electronic device, e.g. a wearable, such as a watch or other wrist-worn electronic device. An accessory device may be a docking station. The docking station may be configured to electrically and/or mechanically couple the monitor device to the docking station. The docking station may be configured for charging the monitor device and/or configured for transferring data between the monitor device and the docking station. The personal care system may comprise a server device. The server device may be operated and/or controlled by the personal care appliance manufacturer and/or a service centre.

The present disclosure provides a personal care system and devices thereof, such as a personal care appliance, e.g. an ostomy appliance or a wound dressing, a monitor device, and optionally one or more accessory devices which either alone or together facilitate reliable determination and monitoring of the nature, severity and rapidness of moisture propagation in the personal appliance, such as in an adhesive material provided for attaching a base plate of an ostomy appliance to the skin surface of a user or in an absorbent core of the wound dressing.

The personal care system may be an ostomy system. Thus, the personal care appliance may be an ostomy appliance.

The personal care system may be a wound dressing system. Thus, the personal care appliance may be a wound dressing appliance also denoted wound dressing. A wound dressing system and devices thereof are provided, such as a wound dressing, a monitor device, and optionally one or more accessory devices which either alone or together facilitate reliable monitoring of the wound dressing and operating state thereof. Accordingly, the wound dressing system and devices thereof enable providing information to the user about the operating state of the wound dressing, and in turn optionally enable providing an indication to the user or a caretaker of the remaining time frame for replacing the wound dressing without experiencing leakage and/or to provide optimum wound healing conditions.

The personal care system may be a catheter system. Thus, the personal care appliance may be a catheter appliance.

The personal care system comprises one or more of a personal care appliance, a monitor device, and one or more accessory devices as described herein.

Depending on the nature of the pattern of moisture propagation in the personal care appliance, the personal care system and devices thereof enable providing information to the user about the status and/or a type of failure, and in turn enable providing an indication to the user of the severity and thus the remaining time frame for replacing the personal care appliance without experiencing severe leakage and/or skin damage and/or to improve wound healing.

In particular, the present disclosure ensures or facilitates that essential data related to the monitoring of the personal care appliance are not lost or at least maintained in the personal care system during connection loss. Further, the present disclosure provides that information to the user about the status and/or a type of failure in the personal care appliance is provided even in case of connection loss in the system. The present disclosure allows higher flexibility to a user, e.g. in scenarios where the user does not have access to the primary accessory device, e.g. during work-out, shopping, work, etc.

It is as important aspect of the present disclosure that a personal care system with redundancy in accessory device functionality is provided.

The ostomy appliance comprises a base plate and an ostomy pouch (also referred to as an ostomy bag). The ostomy appliance may be a colostomy appliance, an ileostomy appliance or a urostomy appliance. The ostomy appliance may be a two-part ostomy appliance, i.e. the base plate and the ostomy pouch may be releasably coupled e.g. with a mechanical and/or an adhesive coupling, e.g. to allow that a plurality of ostomy pouches can be utilized (exchanged) with one base plate. Further, a two-part ostomy appliance may facilitate correct application of the base plate to skin, e.g. to an improved user sight of the stomal region. The ostomy appliance may be a one-part ostomy appliance, i.e. the base plate and the ostomy pouch may be fixedly attached to each other. The base plate is configured for coupling to a user's stoma and/or skin surrounding the stoma, such as a peristomal skin area. The ostomy appliance may comprise an electrode assembly or the ostomy system optionally comprises an electrode assembly mountable on a proximal side of the base plate of the ostomy appliance. The electrode assembly, also denoted sensor assembly or sensor patch, comprises a plurality of electrodes optionally arranged on a distal side of a first adhesive layer of the ostomy appliance or on a distal side of a first adhesive layer of the electrode assembly, the plurality of electrodes forming a plurality of sensors (electrode pairs). The ostomy appliance/electrode assembly may comprise a monitor interface for connecting electrodes of the electrode assembly to terminals of the first interface of the monitor device.

The wound dressing appliance comprises a top layer, a first adhesive layer with a proximal surface configured for attachment of the wound dressing to the skin surface of a user; an absorbent core layer; and an electrode assembly comprising a plurality of electrodes optionally arranged on a distal side of the absorbent core layer, the plurality of electrodes forming a plurality of sensors (electrode pairs). The top layer is optionally on a distal side of the electrode assembly. The wound dressing may comprise a monitor interface for connecting electrodes of the electrode assembly to terminals of the first interface of the monitor device.

A monitor device for a personal care system comprising a personal care appliance, the monitor device, and one or more accessory devices is disclosed, the monitor device comprising a processor; a memory connected to the processor; a first interface connected to the processor, the first interface configured for connecting the monitor device to the personal care appliance; and a second interface comprising a transceiver module connected to the processor and configured for connecting the monitor device to the one or more accessory devices of the personal care system. The monitor device is configured to establish a connection between the monitor device and at least one of the one or more accessory devices; determine whether a primary storing criterion, e.g. based on a quality of the connection, is satisfied; and in accordance with a determination that the primary storing criterion is satisfied, store primary monitor data in the memory according to a primary storing scheme.

A storing scheme optionally defines one or more storing parameters, such as a storing frequency and/or a data size of monitor data stored in a storing operation, for storing monitor data in the memory. A storing scheme optionally defines one or more parts of monitor data to be stored in accordance with the storing scheme. The primary storing scheme may define a primary storing frequency for storing monitor data in the memory according to the primary storing scheme. The primary storing scheme may define a primary data size of monitor data stored in a storing operation in the memory according to the primary storing scheme.

The monitor data may comprise appliance data (also denoted a first part of monitor data) optionally indicative of a physical condition of the personal care appliance. The appliance data may be ostomy data indicative of a physical condition of the ostomy appliance, such as a physical condition of a base plate of the ostomy appliance and/or an electrode assembly. The appliance data may be wound dressing data indicative of a physical condition of the wound dressing appliance, such as a physical condition of an absorbent core layer of the wound dressing appliance. The primary monitor data may comprise primary appliance data and/or the secondary monitor data may comprise secondary appliance data. The primary appliance data may be different from the secondary monitor data.

The appliance data, such as the primary appliance data and/or the secondary appliance data, may comprise first appliance sensor data obtained from or derived from a first sensor (e.g. a first electrode pair) of the personal care appliance. The first sensor may be an outer or outermost sensor of an ostomy appliance/electrode assembly. The first sensor may be a sensor arranged at or near a periphery of an absorbent core of a wound dressing appliance. The appliance data, such as the primary appliance data and/or the secondary appliance data, may comprise second appliance sensor data obtained from or derived from a second sensor (e.g. a second electrode pair) of the personal care appliance. The second sensor may be an inner or innermost sensor of an ostomy appliance/electrode assembly. The second sensor may be a sensor centrally located on an absorbent core of a wound dressing appliance. The appliance data, such as the primary appliance data and/or the secondary appliance data, may comprise third appliance sensor data obtained from or derived from a third sensor (e.g. a third electrode pair) of the personal care appliance. The third sensor may be an inner or innermost sensor of an ostomy appliance/electrode assembly. The appliance data, such as the primary appliance data and/or the secondary appliance data, may comprise fourth appliance sensor data obtained from or derived from a fourth sensor (e.g. a fourth electrode pair) of the personal care appliance. The fourth sensor may be an inner or innermost sensor of an ostomy appliance/electrode assembly. The appliance data, such as the primary appliance data and/or the secondary appliance data, may comprise fifth appliance sensor data obtained from or derived from a fifth sensor (e.g. a fifth electrode pair) of the personal care appliance. The fifth sensor may be a sensor of an ostomy appliance/electrode assembly arranged between an inner sensor and an outermost sensor.

In one or more exemplary monitor devices, the primary storing criterion based on a quality of the connection is satisfied when it is determined that the quality of the connection is below a threshold. The primary storing criterion being satisfied may indicate that the connection is lost or that the connection has a low quality or does not have a satisfactory quality to transmit monitor data to the accessory device. In other words, the monitor device is optionally configured to store the monitor data in the memory upon determination of no or low-quality connection to the accessory device. For example, the primary storing criterion, also denoted SC_1, may be based on a primary connection parameter, CP_1, associated with the connection and being indicative of a quality of the connection.

The primary storing criterion SC_1 may be given as:

$$SC\_1: CP\_1 < TH\_S\_1,$$

wherein CP_1 is the primary connection parameter and TH_S_1 is a primary storing threshold. The primary connection parameter CP_1 may be a signal strength indicator, such as a received signal strength indicator (RSSI) or a received channel power indicator (RCPI). The primary connection parameter CP_1 may be a signal-to-noise ratio.

The primary storing criterion SC_1 may be given as:

$$SC\_1: CP\_1 > TH\_S\_1,$$

wherein CP_1 is the primary connection parameter indicative of errors in the connection (large number of errors indicating no or poor connection), such as an error rate (such as a bit error rate or a frame error rate), a number of non-acknowledgements (NACKs), and/or a number of retransmissions, and TH_S_1 is a primary storing threshold.

In one or more exemplary monitor devices, to determine whether a primary storing criterion, e.g. based on a quality of the connection, is satisfied may comprise to determine or obtain a primary connection parameter, CP_1, based on one or more connection parameters, and to compare the primary connection parameter with a primary storing threshold TH_S_1.

The primary connection parameter may be based on one or more connection parameters, such as signal-to-noise ratio, an error rate (such as a bit error rate, and/or a frame error rate), a number of non-acknowledgements (NACKs), and/or a number of retransmissions. In one or more exemplary monitor devices, in accordance with a determination that the primary storing criterion is satisfied, the monitor device does not transmit monitor data any longer or forgo to transmit monitor data to the accessory device. In other words, the monitor device may be configured to determine whether the connection to the accessory device is lost by determining whether the primary storing criterion based on the quality of the connection is satisfied. Stated differently, the primary storing criterion based on a quality of the connection is satisfied when it is determined that the quality of the connection is degraded (e.g. poor) and/or reduced, leading to a loss of connection to the accessory device. Thus, the monitor device is configured to store monitor data in the memory in case the connection to the accessory device is of low quality, e.g. lost or degraded.

The monitor device may be configured to, in accordance with a determination that the primary storing criterion is satisfied, determine the primary storing scheme.

In one or more exemplary monitor devices, the monitor device is configured to, in accordance with a determination that the primary storing criterion is satisfied, select or determine the primary storing scheme from a plurality of storing schemes. The plurality of storing schemes may comprise two, three, four, or more storing schemes, such as at least five storing schemes. The plurality of storing schemes comprises a first storing scheme and a second storing scheme.

In one or more exemplary monitor devices, the monitor device is configured to transmit monitor data to the accessory device, wherein to transmit monitor data to the accessory device comprises to store monitor data in the memory according to a transmit storing scheme, e.g. as a part of buffering the monitor data (real-time monitor data) to be transmitted. The primary storing scheme is different from the transmit storing scheme. The primary storing scheme may have a primary storing frequency smaller than a transmit storing frequency of the transmit storing scheme and/or the primary storing scheme may have a first data size larger than a transmit data size of the transmit storing scheme.

The monitor data transmitted to the accessory device may comprise appliance data that are not stored in the memory according to the primary storing scheme and/or a secondary storing scheme. For example, appliance sensor data obtained from or derived from one or more appliance sensors being part of monitor data transmitted to the accessory device may not be stored in the memory according to the primary storing scheme and/or secondary storing scheme. Accordingly, the primary monitor data may be a reduced data set compared to the real-time monitor data that are transmitted to the accessory device during normal connection and optionally stored according to the transmit storing scheme. Thereby, optimum or improved usage of the limited memory capacity in the monitor device is provided.

The primary monitor data may comprise compressed appliance sensor data, such as compressed appliance sensor data for one or more sensors that are not regarded as critical, such as an inner sensor of an ostomy appliance or wound dressing. Appliance sensor data for one or more sensors that are not regarded as critical may be omitted in the primary monitor data. The primary monitor data may comprise monitor data different from the monitor data transmitted when the connection is ok/satisfactory (also denoted real-time monitor data). For example, the real-time monitor data may comprise appliance sensor data, such as one or more of second appliance sensor data, third appliance sensor data, fourth appliance sensor data, and fifth appliance sensor, that are not included in the primary monitor data. Optionally, the primary monitor data may comprise appliance sensor data that are not included in the real-time monitor data. For example, the processor of the monitor device may be configured to determine one or more parameters based on the appliance data and include the parameters in the primary monitor data in accordance with a determination that the first storing criterion is satisfied.

In one or more exemplary monitor devices, to store primary monitor data may comprise compressing and/or deleting monitor data stored in accordance with the transmit storing scheme.

In one or more exemplary monitor devices, to select the primary storing scheme is based on a first parameter indicative of time since a quality of the connection is less than a threshold. In one or more exemplary monitor devices, to select the primary storing scheme is based on a first parameter indicative of time since a determination that the primary storing scheme was satisfied. In one or more exemplary monitor devices, to select the primary storing scheme comprises to select a first storing scheme as the primary storing scheme if the first parameter indicative of time since a determination that the primary storing scheme was satisfied is indicative of a small time, e.g. if the first parameter is less than a first time threshold, and/or to select a second storing scheme as the primary storing scheme if the first parameter indicative of time since a determination that the primary storing scheme was satisfied is indicative of a long time, e.g. if the first parameter is larger than a second time threshold. The first time threshold may be different from the second time threshold.

In one or more exemplary monitor devices, to select the primary storing scheme is based on a second parameter indicative of available memory capacity of the memory. In one or more exemplary monitor devices, to select the primary storing scheme comprises to select a first storing scheme as the primary storing scheme if the second parameter indicative of available memory capacity is indicative of a large memory capacity, e.g. if the second parameter is larger than a first memory threshold, and/or to select a second storing scheme as the primary storing scheme if the second parameter indicative of available memory capacity is indicative of a small or reduced memory capacity, e.g. if the second parameter is less than a second memory threshold.

In one or more exemplary monitor devices, to select the primary storing scheme is based on both the first parameter and the second parameter. Thereby improved storing of monitor data may be provided.

In one or more exemplary monitor devices, to select the primary storing scheme is based on an operating state of the personal care appliance. For example, a first operating state of the personal care appliance, e.g. requiring high attention, may trigger selection of a first storing scheme as the primary storing scheme, while a second operating state, e.g. requiring no or little attention, may trigger selection of a second storing scheme as the primary storing scheme, wherein the first storing scheme has a first storing frequency larger than a second storing frequency of the second storing scheme and/or wherein the first storing scheme has a first data size larger than a second data size of the second storing scheme.

In one or more exemplary monitor devices, the monitor device is configured to determine whether a secondary storing criterion, e.g. based on an available memory capacity of the memory, is satisfied; and in accordance with a determination that the secondary storing criterion is satisfied, store secondary monitor data in the memory according to a secondary storing scheme.

The secondary storing scheme may define a secondary storing frequency for storing monitor data in the memory according to the secondary storing scheme. The secondary storing scheme may define a secondary data size of monitor data stored in a storing operation in the memory according to the secondary storing scheme. The primary storing scheme may be different from the secondary storing scheme. For example, the secondary storing frequency of the secondary storing scheme may be less than the primary storing frequency of the primary storing scheme and/or the secondary data size may be smaller than the primary data size. In other words, the amount of data stored during the primary storing scheme may be larger than the amount of data stored during the secondary storing scheme (over the same time). Thus, the primary monitor data stored per time unit may be more than the secondary monitor data stored per time unit.

The primary monitor data may comprise appliance data that are not included in the secondary monitor data. For example, appliance sensor data obtained from or derived from one or more appliance sensors being part of the primary monitor data may not be included in the secondary monitor data. Accordingly, the secondary monitor data may be a reduced data set compared to the primary monitor data. Thereby, optimum or improved usage of the limited memory capacity in the monitor device is provided.

The secondary monitor data may comprise compressed appliance sensor data, such as compressed appliance sensor data for one or more sensors that are not regarded as critical, such as an inner sensor of an ostomy appliance or wound dressing. Appliance sensor data for one or more sensors that are not regarded as critical may be omitted in the secondary monitor data. For example, the primary monitor data may comprise appliance sensor data, such as one or more of second appliance sensor data, third appliance sensor data, fourth appliance sensor data, and fifth appliance sensor, that are not included in the secondary monitor data stored in the memory.

In one or more exemplary monitor devices, the monitor device is configured to determine whether a tertiary storing criterion, e.g. based on an operating state of the personal care appliance, is satisfied; and in accordance with a determination that the tertiary storing criterion is satisfied, store tertiary monitor data in the memory according to a tertiary storing scheme.

The tertiary storing scheme may define a tertiary storing frequency for storing monitor data in the memory according to the tertiary storing scheme. The tertiary storing scheme may define a tertiary data size of monitor data stored in a storing operation in the memory according to the tertiary storing scheme. The tertiary storing scheme may be different from the secondary storing scheme and/or different from the primary storing scheme. For example, the tertiary storing frequency of the secondary storing scheme may be larger than the primary storing frequency of the primary storing scheme and/or the tertiary data size may be larger than the primary data size. In other words, the amount of data stored during the primary storing scheme may be less than the amount of data stored during the tertiary storing scheme (over the same time), e.g. in case the operating state of the personal care appliance changes from a first operating state, e.g. requiring no or little attention, to a second operating state, e.g. requiring high attention. Thus, the primary monitor data stored per time unit may be less than the tertiary monitor data stored per time unit. The tertiary storing criterion being satisfied may indicate that the operating state of the personal care appliance indicates that high attention is required by the user or that operating state of the personal care appliance indicates an increase in the level of required attention by the user.

The secondary storing criterion being satisfied may indicate that the available memory capacity of the memory is low. In other words, the monitor device is optionally configured to dynamically adapt storing of the monitor data in the memory in turn resulting in improved utilisation of the memory resources in the monitor device. For example, the secondary storing criterion, also denoted SC_2, may be based on a secondary storage parameter, SP_2, associated with memory and being indicative of available memory capacity of the memory.

The secondary storing criterion SC_2 may be given as:

SC_2: SP_2<TH_M_2, wherein SP_2 is the secondary storage parameter and TH_M_2 is a secondary memory threshold.

In one or more exemplary monitor devices, to determine whether a secondary primary storing criterion is satisfied may comprise to determine or obtain a secondary storage parameter, SP_2, e.g. based on a size of the memory and/or the amount of data stored in the memory since a determination that the primary storing criterion was satisfied, and to compare the secondary storage parameter with a secondary memory threshold TH_M_2.

In one or more exemplary monitor devices, to store secondary monitor data comprises compressing primary monitor data in the memory. In other words, the monitor device may be configured to free up memory by compressing the primary monitor data stored during application of the primary storing scheme and store the compressed primary monitor data in the memory. The compressed primary monitor data may be over-written on a part of the primary monitor data.

In one or more exemplary monitor devices, to store secondary monitor data comprises deleting, e.g. by overwriting, primary monitor data from the memory. To store secondary monitor data may comprise selecting a part of the primary monitor data, e.g. the oldest primary monitor data and/or primary monitor data of less importance/low priority, and overwriting the selected part of the primary monitor data with the secondary monitor data.

In one or more exemplary monitor devices, to store secondary monitor data may comprise compressing and/or deleting monitor data stored in accordance with the transmit storing scheme.

In one or more exemplary monitor devices, the monitor device is configured to, in accordance with a determination that the secondary storing criterion is satisfied, select the secondary storing scheme from the plurality of storing schemes or determine the secondary storing scheme.

In one or more exemplary monitor devices, to select the secondary storing scheme is based on a first parameter indicative of time since a quality of the connection is less than a threshold. In one or more exemplary monitor devices, to select the secondary storing scheme is based on a first parameter indicative of time since a determination that the primary storing scheme was satisfied.

In one or more exemplary monitor devices, to select the secondary storing scheme is based on a second parameter indicative of available memory capacity of the memory. In one or more exemplary monitor devices, to select the secondary storing scheme comprises to select a first storing scheme as the secondary storing scheme if the second parameter indicative of available memory capacity is indicative of a large memory capacity, e.g. if the second parameter is larger than a first memory threshold, and/or to select a second storing scheme as the primary storing scheme if the second parameter indicative of available memory capacity is indicative of a small or reduced memory capacity, e.g. if the second parameter is less than a second memory threshold. In one or more exemplary monitor devices, to select the secondary storing scheme is based on both the first parameter and the second parameter. In one or more exemplary monitor devices, to select the secondary storing scheme is based on an operating state of the personal care appliance.

In one or more exemplary monitor devices, the monitor device is configured to determine whether a transmission criterion based on the quality of the connection is satisfied; and in accordance with a determination that the transmission criterion is satisfied, transmit monitor data in the memory to the accessory device. The transmission criterion being satisfied may indicate that the connection is resumed and/or returns to a satisfactory quality. In other words, the monitor device is optionally configured to transmit the monitor data in the memory stored during a time period of no or low-quality connection to the accessory device upon determination of reestablishment of the connection. For example, the transmission criterion, also denoted TC, may be based on a connection parameter, CP, associated with the connection and being indicative of a quality of the connection.

The transmission criterion may be given as:

TC: CP>TH_T, wherein CP is the connection parameter and TH_T is a transmission threshold. The connection parameter CP may be a signal strength indicator, such as a received signal strength indicator (RSSI) or a received channel power indicator (RCPI). The connection parameter CP may be a signal-to-noise ratio.

The transmission criterion may be given as:

TC: CP>TH_T, wherein CP is the connection parameter indicative of errors in the connection (large number of errors indicating no or poor connection), such as an error rate (such as a bit error rate or a frame error rate), a number of non-acknowledgements (NACKs), and/or a number of retransmissions, and TH_T is a transmission threshold.

In one or more exemplary monitor devices, to transmit monitor data in the memory to the accessory device comprises to transmit the secondary monitor data, and after transmitting the secondary monitor data, to transmit the primary monitor data. Thereby, the accessory device receiving the stored monitor data is able to determine and communicate a current operating state fast, as the secondary monitor data may comprise the most recent and/or most critical data.

In one or more exemplary monitor devices, the memory is a flash memory of the transceiver module, and wherein to store primary monitor data in the memory according to a primary storing scheme is based on one or more control parameters output from the processor to the transceiver module. To store secondary monitor data in the memory according to a secondary storing scheme may be based on one or more control parameters output from the processor to the transceiver module.

In one or more exemplary monitor devices, the primary monitor data comprises primary ostomy data obtained from an ostomy appliance being the personal care appliance via the first interface or primary wound dressing data obtained from a wound dressing being the personal care appliance via the first interface. In one or more exemplary monitor devices, the secondary monitor data comprises secondary ostomy data obtained from an ostomy appliance being the personal care appliance via the first interface or secondary wound dressing data obtained from a wound dressing being the personal care appliance via the first interface.

Further, a method of operating a monitor device for a personal care system comprising a personal care appliance, the monitor device, and one or more accessory devices is disclosed, the monitor device comprising a processor; a memory connected to the processor; a first interface connected to the processor, the first interface configured for connecting the monitor device to the personal care appliance; and a second interface comprising a transceiver module connected to the processor and configured for connecting the monitor device to one or more accessory devices of the personal care system. The method comprises establishing a connection between the monitor device and at least one of the one or more accessory devices; determining whether a primary storing criterion, e.g. based on a quality of the connection, is satisfied; and in accordance with a determination that the primary storing criterion is satisfied, storing primary monitor data in the memory according to a primary storing scheme.

In one or more exemplary methods of operating a monitor device, determining whether the primary storing criterion based on a quality of the connection is satisfied comprises determining whether the quality of the connection is below a threshold.

In one or more exemplary methods of operating a monitor device, the method comprises transmitting monitor data to the accessory device, wherein transmitting monitor data to the accessory device optionally comprises storing monitor data in the memory according to a transmit storing scheme. The primary storing scheme is different from and optionally requires less memory than the transmit storing scheme. The primary storing scheme may have a primary storing frequency smaller than a transmit storing frequency of the transmit storing scheme and/or the primary storing scheme may have a first data size larger or smaller than a transmit data size of the transmit storing scheme.

In one or more exemplary methods of operating a monitor device, storing primary monitor data may comprise compressing and/or deleting monitor data stored in accordance with the transmit storing scheme.

In one or more exemplary methods of operating a monitor device, the method comprising, in accordance with a determination that the primary storing criterion is satisfied, selecting the primary storing scheme from a plurality of storing schemes.

In one or more exemplary methods of operating a monitor device, selecting the primary storing scheme is based on a first parameter indicative of time since a quality of the connection is less than a threshold.

In one or more exemplary methods of operating a monitor device, selecting the primary storing scheme is based on a second parameter indicative of available memory capacity of the memory.

In one or more exemplary methods of operating a monitor device, selecting the primary storing scheme is based on an operating state of the personal care appliance.

In one or more exemplary methods of operating a monitor device, the method comprises determining whether a secondary storing criterion, e.g. based on an available memory capacity of the memory, is satisfied; and in accordance with a determination that the secondary storing criterion is satisfied, storing secondary monitor data in the memory according to a secondary storing scheme.

In one or more exemplary methods of operating a monitor device, storing secondary monitor data comprises compressing primary monitor data in the memory.

In one or more exemplary methods of operating a monitor device, storing secondary monitor data comprises deleting primary monitor data from the memory.

In one or more exemplary methods of operating a monitor device, storing secondary monitor data may comprise compressing and/or deleting monitor data stored in accordance with the transmit storing scheme.

In one or more exemplary methods of operating a monitor device, the method comprises determining whether a tertiary storing criterion, also denoted SC_3, e.g. based on an operating state of the personal care appliance, is satisfied; and in accordance with a determination that the tertiary storing criterion is satisfied, storing tertiary monitor data in the memory according to a tertiary storing scheme.

In one or more exemplary methods of operating a monitor device, the method comprises determining whether a transmission criterion based on the quality of the connection is satisfied; and in accordance with a determination that the transmission criterion is satisfied, transmitting monitor data in the memory to the accessory device.

In one or more exemplary methods of operating a monitor device, transmitting monitor data in the memory to the accessory device comprises to transmit the secondary monitor data, and after transmitting the secondary monitor data, to transmit the primary monitor data.

In one or more exemplary methods of operating a monitor device, the memory is a flash memory of the transceiver module, and storing primary monitor data in the memory according to a primary storing scheme is based on one or more control parameters from the processor to the transceiver module. Storing secondary monitor data in the memory according to a secondary storing scheme may be based on one or more control parameters from the processor to the transceiver module.

In one or more exemplary methods of operating a monitor device, the personal care appliance is an ostomy appliance, and the method comprising obtaining primary ostomy data from the ostomy appliance and including the primary ostomy data in the primary monitor data; or the personal care appliance is a wound dressing, and the method comprising obtaining primary wound dressing data from the wound dressing and including the primary wound dressing data in the primary monitor data.

It is to be noted that descriptions of the monitor device being configured to perform acts also apply to the corresponding acts in the method of operating a monitor device and vice versa.

Also disclosed is a computer readable storage medium storing one or more programs, the one or more programs comprising instructions, which when executed by a monitor device with an interface, a memory and a processor cause the monitor device to be configured to operate in accordance with methods of operating a monitor device as described herein.

The present disclosure provides an accessory device for a personal care system. The personal care system comprises a personal care appliance, a monitor device, and the accessory device. The accessory device comprises a processor; a memory connected to the processor; and an interface configured to connect the accessory device to the monitor device of the personal care system, the interface comprising a transceiver module connected to the processor. The accessory device is configured to establish a connection between the monitor device and the accessory device. The accessory device is configured to receive monitor data from the monitor device. The accessory device is configured to determine an operating state of the personal care appliance based on the monitor data. The accessory device is configured to determine whether a primary criterion, e.g. based on a quality of the connection, is satisfied. The accessory device is configured to, in accordance with a determination that the primary criterion is not satisfied, communicate a first indication indicative of the quality of the connection.

The disclosed accessory device is capable of communicating a first indication indicative of a quality of connection to the monitor device. The present disclosure improves the reliability of the monitoring performed by the personal care system, by communicating the first indication indicative of the quality of connection when a quality of the connection is not satisfactory. This permits to notify appropriately the user and to start potentially estimating the operating state without real-time current monitor data. For example, communication of the first indication indicative of a quality of connection to the monitor device helps reducing the risk of a user experiencing a leakage (e.g. output leakage between a user's skin and the baseplate of the ostomy appliance) from an ostomy appliance in a planned activity. For example, communication of the first indication indicative of a quality of connection to the monitor device helps reducing the risk of a user experiencing a wet wound due to saturated fluid in an absorbent core layer of a wound dressing appliance. In particular, determination and communication the first indication indicative of an estimated operating state, and possibly with a latest operating state, according to the present disclosure is performed based on monitor data indicative of a condition of the ostomy appliance which may not be visible to the user.

It is an advantage of the present disclosure that a user of a personal care appliance or a health care professional is able to monitor and plan the use of the personal care appliance with daily life.

For example, the accessory device is configured to, in accordance with a determination that the primary criterion is not satisfied, communicate the first indication, e.g. to the user, e.g. via an output device (such as a display and/or a loudspeaker). In one or more exemplary embodiments, the first indication may be communicated by sound.

For example, the accessory device is configured to, in accordance with a determination that the primary criterion is not satisfied, communicate the first indication, e.g. to another device, e.g. an external device (such as wearable device and/or a server device).

In one or more exemplary accessory devices, the primary criterion based on a quality of the connection is not satisfied when it is determined that the quality of the connection is not above a primary connection threshold.

In one or more exemplary accessory devices, the primary criterion based on a quality of the connection is not satisfied when it is determined that the quality of the connection is below a primary connection threshold. The primary criterion not being satisfied may indicate that the connection is lost or that the connection has a low quality or does not have a satisfactory quality to receive monitor data from the monitor device. In other words, the monitor device is optionally configured to communicate the first indication upon determination of no or low-quality connection to the monitor device. For example, the primary criterion, also denoted $C\_1$, may be based on one or more connection parameters associated with the connection and being indicative of a quality of the connection, such as a signal strength indicator, e.g. a received signal strength indicator (RSSI) or a received channel power indicator (RCPI), signal-to-noise ratio, an error rate, e.g. a bit error rate, and/or a frame error rate, a number of non-acknowledgements (NACKs), and/or a number of retransmissions. In other words, the accessory device may be configured to determine whether the connection to the monitor device is lost by determining whether the primary criterion based on the quality of the connection is satisfied. Stated differently, the primary criterion based on a quality of the connection is not satisfied when it is determined that the quality of the connection is degraded (e.g. poor) and/or reduced, leading to a loss of connection to the monitor device. Thus, the accessory device is configured to communicate the first indication in case the connection to the monitor device is of low quality, e.g. lost or degraded.

The primary criterion $C\_1$ may be given as:

$$C\_1: CP>TH\_C\_1,$$

wherein CP is the connection parameter and $TH\_C\_1$ is a primary connection threshold. The connection parameter CP may be a signal strength indicator, such as a received signal strength indicator (RSSI) or a received channel power indicator (RCPI). The connection parameter CP may be a signal-to-noise ratio.

The primary criterion $C\_1$ may be given as:

$$C\_1: CP<TH\_C\_1,$$

wherein CP is the connection parameter indicative of errors in the connection (large number of errors indicating no or poor connection), such as an error rate (such as a bit error rate or a frame error rate), a number of non-acknowledgements (NACKs), and/or a number of retransmissions, and $TH\_C\_1$ is a primary connection threshold.

In one or more exemplary accessory devices, to determine whether a primary criterion, e.g. based on a quality of the connection, is satisfied may comprise to determine or obtain one or more connection parameters, and to compare the connection parameter with a primary connection threshold $TH\_C\_1$.

The connection parameter may be based on one or more of a signal strength indicator, e.g. a received signal strength indicator (RSSI) or a received channel power indicator (RCPI), signal-to-noise ratio, an error rate, e.g. a bit error rate, and/or a frame error rate, a number of non-acknowledgements (NACKs), and/or a number of retransmissions.

For example, the primary criterion based on a quality of the connection is not satisfied when it is determined that the quality of the connection is equal or below the primary connection threshold. The primary connection threshold may be associated with or based on one or more connection parameters, such as signal to noise ratio, an error rate (such as a bit error rate, and/or a frame error rate), a number of non-acknowledgements (NACKs), and/or a number of retransmissions. In one or more exemplary accessory devices, in accordance with a determination that the primary criterion is not satisfied, the accessory device does not receive monitor data any longer or forgo to receive the monitor data. In other words, the accessory device may be configured to determine whether the connection to the monitor device is lost by determining whether the primary criterion based on the quality of the connection is satisfied. Stated differently, the primary criterion based on a quality of the connection is not satisfied when it is determined that the quality of the connection is degraded (e.g. poor) and/or reduced, leading to a loss of connection to the monitor device.

In one or more exemplary accessory devices, the accessory device is configured to, in accordance with a determination that the primary criterion is not satisfied, select, from a plurality of indications, the first indication indicative of the quality of the connection. In one or more exemplary accessory devices, the first indication is indicative of the operating state at a time where the primary criterion based on the quality of the connection is not satisfied. For example, the first indication is indicative of the operating state at a time where the connection is lost and/or degraded and/or interrupted.

The accessory device is optionally configured to, in accordance with a determination that the primary criterion is not satisfied, determine, such as select, obtain, and/or generate, the first indication indicative of the quality of the connection. For example, the first indication is indicative of the operating state at a time where the connection is lost and/or degraded and/or interrupted. The first indication may be indicative of a time passed since a determination that the primary criterion was not satisfied, e.g. a time passed since the connection was lost and/or degraded and/or interrupted.

For example, the first indication may be selected from the plurality of indications comprising an indication indicative of the connection lost and/or degraded, and an indication indicative of the operating state at a time where the primary criterion based on the quality of the connection is not satisfied.

In one or more exemplary accessory devices, to select the first indication indicative of the quality of the connection comprises to determine an estimated operating state of the personal care appliance based on one or more previous operating states of the personal care appliance. The one or more previous operating states of the personal care appliance are determined by the accessory device before the time where the primary criterion based on the quality of the connection is not satisfied (e.g. before the time where the connection is lost).

In one or more exemplary accessory devices, to determine the estimated operating state of the personal care appliance based on one or more previous operating states of the personal care appliance comprises to predict the estimated operating state of the personal care appliance based on one or more previous operating states of the personal care appliance. In one or more exemplary accessory devices, the first indication is indicative of the estimated operating state.

The processor may be configured to determine the estimated operating state based on one or more previous operating states, such as based on one or more operating states previously determined by the accessory device (i.e. prior to loss/degradation of connection). The one or more operating states previously determined by the accessory device may relate the similar personal care appliances as the one currently used by the user. Optionally, one or more operating states previously determined by the accessory device may relate the different personal care appliances as the one currently used by the user, which have the characteristics and/or components which are the same as the one currently used by the user.

The processor of the accessory device may be configured to determine the estimated operating state as a future operating state of the personal care appliance based on one or more previous operating states, such as based on one or more (future and/or current) operating states previously determined by the accessory device.

It may be envisaged that the processor of the accessory device may be configured to predict the estimated operating state of the personal care appliance by deriving a trend or a function of an operating state and/or the monitor data over the time period, e.g. for the similar personal care appliances as the one currently used by the user, or for similar base plates as the currently used one. The time period may include a time period up to and possibly including a current time. The time period may include a time period from a start time of use of any personal care appliances, to the current time of determination of the estimated operating state. The time period may include a time period from a start time of the loss of connection to the current time. The time period may include a time window that periodically occurs, such as a morning time period, an afternoon time period, a night time period, a daily time period, a weekly time period, etc.

The processor of the accessory device may be configured to predict the estimated operating state based on a parameter characterizing a product type of the personal care appliance. The processor of the accessory device may be configured to predict (such as to determine) the estimated operating state based on monitor data obtained for similar product types of personal care appliances previously used by the user.

In one or more exemplary accessory devices, the accessory device is configured to, in accordance with a determination that the primary criterion is not satisfied, communicate the first indication indicative of the quality of the connection, by displaying, on a display of the accessory device, a first user interface object representative of the first indication. The first user interface object may be displayed as one or more media, such as text, graphic and/or video.

The accessory device may comprise the display configured to display a user interface. The display may comprise a touch sensitive surface. A user interface comprises one or more user interface objects. A user interface may be referred to as a user interface screen.

A user interface object refers herein to a graphical representation of an object that is displayed on the display of the accessory device. The user interface object may be user-interactive, or selectable by a user input. For example, an image (e.g., icon), a button, and text (e.g., hyperlink) each optionally constitute a user interface object. The user interface object may form part of a widget. A widget may be seen as a mini-application that may be used by the user and created by the user. A user interface object may comprise a prompt, application launch icon, and/or an action menu. An input, such as first input and/or second input, may comprise a touch (e.g. a tap, a force touch, a long press), a and/or movement of contact (e.g. a swipe gesture, e.g. for toggling). The movement on contact may be detected by a touch sensitive surface, e.g. on a display of an accessory device. Thus, the display may be a touch sensitive display. An input, such as first input and/or second input, may comprise a lift off. An input, such as first input and/or second input, may comprise a touch and a movement followed by a lift off.

The display of the accessory device may be configured to detect touch (e.g. the display is a touch-sensitive display), the input comprises a contact on the touch sensitive display. A touch-sensitive display provides an input interface and an output interface between the accessory device and a user. A processor of the accessory device may be configured to receive and/or send electrical signals from/to touch-sensitive display. A touch-sensitive display is configured to display visual output to the user. The visual output optionally includes graphics, text, icons, video, and any combination thereof (collectively termed "graphics"). For example, some or all of the visual output may be seen as corresponding to user interface objects.

The processor of the accessory device may be configured to display, on the display, one or more user interfaces, such as user interface screens, including a first user interface and/or a second user interface. A user interface may comprise one or more, such as a plurality of user interface objects. For example, the first user interface may comprise a first primary user interface object and/or a first secondary user interface object. A second user interface may comprise a second primary user interface object and/or a second secondary user interface object. A user interface object, such as the first primary user interface object and/or the second primary user interface object, may represent an operating state of the personal care appliance.

In one or more exemplary accessory devices, to communicate the first indication comprises to display, on a visual interface (e.g. a display) of the accessory device, a user interface comprising a user interface object representative of the first indication, such as a first user interface object representative of the first indication indicative of the quality of the connection and/or representative of a first operating state of the personal care appliance, and/or representative of a second operating state of the personal care appliance.

In one or more exemplary accessory devices, the first user interface object representative of the first indication comprises a first primary user interface object representative of the first indication, and/or a first primary user interface object representative one or more operating states.

For example, the first user interface object may comprise one or more visual indicators representative of the first indication, such as a first visual indicator, a second visual indicator, a third visual indicator. For example, the visual indicator may be in a shape characterizing the personal care appliance. The visual change may be performed by a change of one or more of: colour, shape, blurring, and animation. For example, the visual indicators may be a text prompt indicating to the user the dynamic internal operating state of the personal care appliance.

In one or more exemplary accessory devices, to communicate the first indication comprises to notify the user via the interface, such as by displaying a notification on a display of the accessory device. The notification may comprise the first user interface object representative of the first indication. The notification may comprise a notification indicator to open an application related to the personal care appliance. The accessory device may be configured to detect an input on the notification indicator. The accessory device may be configured to, in response to the input, opening the application related to the personal care appliance. The accessory device may be configured to, in response to the opening of the application, to display a user interface object representative of an operating state (such as a latest operating state and/or an estimated operating state).

In one or more exemplary accessory devices, the accessory device is configured to determine whether a secondary criterion based on the quality of the connection is satisfied. For example, the secondary criterion based on a quality of the connection may be satisfied when it is determined that the quality of the connection is above a secondary connection threshold. In one or more embodiments, the primary connection threshold is the same as the secondary connection threshold. In one or more embodiments, the primary connection threshold is different from the secondary connection threshold. It may be appreciated that having the primary connection threshold different from the secondary connection threshold may lead to a reduction of a ping pong effect between connection lost and connection re-established, thus reducing the number of indications to the user by avoiding ping pong between the communication of the first indication and the communication of the second indication.

The secondary criterion being satisfied may indicate that the connection is resumed and/or returns to a satisfactory quality. For example, the secondary criterion, also denoted $C\_2$, may be based on a connection parameter, CP, associated with the connection and being indicative of a quality of the connection.

The secondary criterion $C\_2$ may be given as:

$$C\_2: CP > TH\_C\_2,$$

wherein CP is the connection parameter and $TH\_C\_2$ is a secondary connection threshold. The connection parameter CP may be a signal strength indicator, such as a received signal strength indicator (RSSI) or a received channel power indicator (RCPI). The connection parameter CP may be a signal-to-noise ratio.

The secondary criterion $C\_2$ may be given as:

$$C\_2: CP < TH\_C\_2,$$

wherein CP is the connection parameter indicative of errors in the connection (large number of errors indicating no or poor connection), such as an error rate (such as a bit error rate or a frame error rate), a number of non-acknowledgements (NACKs), and/or a number of retransmissions, and $TH\_C\_2$ is a secondary connection threshold.

In one or more exemplary accessory devices, to determine whether a secondary criterion, e.g. based on a quality of the connection, is satisfied may comprise to determine or obtain one or more connection parameters, and to compare the connection parameter with a secondary connection threshold $TH\_C\_2$.

The connection parameter of the secondary criterion may be based on one or more of a signal strength indicator, e.g. a received signal strength indicator (RSSI) or a received channel power indicator (RCPI), signal-to-noise ratio, an error rate, e.g. a bit error rate, and/or a frame error rate, a number of non-acknowledgements (NACKs), and/or a number of retransmissions.

In one or more exemplary accessory devices, the accessory device is configured to in accordance with a determination that the secondary criterion is satisfied (connection resumed or has increased quality), communicate a second indication indicative of the quality of the connection. In one or more exemplary accessory devices, the accessory device is configured to in accordance with a determination that the secondary criterion is satisfied, determine the second indication.

The accessory device is optionally configured to, in accordance with a determination that the secondary criterion is satisfied, determine, such as select, obtain, and/or generate, the second indication indicative of the quality of the connection. For example, the second indication may be indicative of an operating state based on monitor data received from the monitor device after the connection has been resumed (secondary criterion is satisfied), such as based on primary monitor data and/or secondary monitor data stored in the monitor device during loss of connection and received by the accessory device after the connection has been resumed (secondary criterion is satisfied).

In one or more exemplary accessory devices, the second indication is indicative of the operating state at a time where the secondary criterion based on a quality of the connection is satisfied. For example, the second indication is indicative of the operating state at a time where the connection is resumed, such as re-established.

In one or more exemplary accessory devices, the accessory device is configured to, in accordance with a determination that the secondary criterion is satisfied, resume reception of the monitor data from the monitor device. For example, the monitor data comprises one or more of: monitor data accumulated during a period of lost connection until resumption of connection (primary monitor data and/or secondary monitor data stored in the monitor device during lost connection), and real-time monitor data (e.g. "live" monitor data, e.g. monitor data received with little or no delay after resumption of connection).

In one or more exemplary accessory devices, the monitor data comprises primary ostomy data obtained from an ostomy appliance being the personal care appliance via the interface or primary wound dressing data obtained from a wound dressing being the personal care appliance via the interface.

In one or more exemplary accessory devices, the accessory device is configured to, in accordance with a determination that the secondary criterion is satisfied, communicate the second indication indicative of the quality of the connection, by displaying, on the display of the accessory device, a second user interface object representative of the second indication. For example, the second user interface objection may convey: "something happened" or "everything is still good" (etc.) during the period of lost connection. For example, to communicate the second indication may comprise to notify the user via the interface, such as by displaying a notification indicative of the second indication on a display of the accessory device.

The present disclosure provides a method of operating an accessory device for a personal care system. The personal care system comprises a personal care appliance, a monitor device, and the accessory device. The method comprises establishing a connection between the monitor device and the accessory device. The method comprises receiving monitor data from the monitor device. The method comprises determining an operating state of the personal care appliance based on the monitor data. The method comprises determining whether a primary criterion based on a quality of the connection is satisfied. The method comprises, in accordance with a determination that the primary criterion is not satisfied, communicating a first indication indicative of the quality of the connection.

In one or more exemplary methods of operating an accessory device, the primary criterion based on a quality of the connection is not satisfied when it is determined that the quality of the connection is not above a primary connection threshold.

In one or more exemplary methods of operating an accessory device, the method comprises, in accordance with a determination that the primary criterion is not satisfied, selecting, from a plurality of indications, the first indication indicative of the quality of the connection.

In one or more exemplary methods of operating an accessory device, communicating the first indication indicative of the quality of the connection in accordance with a determination that the primary criterion is not satisfied comprises displaying, on a display of the accessory device, a first user interface object representative of the first indication.

In one or more exemplary methods of operating an accessory device, selecting the first indication indicative of the quality of the connection comprises determining an estimated operating state of the personal care appliance based on one or more previous operating states of the personal care appliance.

In one or more exemplary methods of operating an accessory device, determining the estimated operating state of the personal care appliance based on the one or more previous operating states of the personal care appliance comprises predicting the estimated operating state of the personal care appliance based on the one or more previous operating states of the personal care appliance.

In one or more exemplary methods of operating an accessory device, the first indication is indicative of the operating state at a time where the primary criterion based on a quality of the connection is not satisfied.

In one or more exemplary methods of operating an accessory device, the first indication is indicative of the estimated operating state.

In one or more exemplary methods of operating an accessory device, the method comprises determining that a secondary criterion based on the quality of the connection is satisfied.

In one or more exemplary methods of operating an accessory device, the method comprises, in accordance with a determination that the secondary criterion is satisfied, communicating a second indication indicative of the quality of the connection.

In one or more exemplary methods of operating an accessory device, the second indication is indicative of the operating state at a time where the secondary criterion based on the quality of the connection is satisfied. For example, the second indication is optionally indicative of the operating state at a time where the connection is resumed, such as re-established.

In one or more exemplary methods of operating an accessory device, the method comprises resuming reception of the monitor data from the monitor device in accordance with a determination that the secondary criterion is satisfied.

In one or more exemplary methods of operating an accessory device, the monitor data comprises primary ostomy data obtained from an ostomy appliance being the personal care appliance via the interface or wound dressing data obtained from a wound dressing being the personal care appliance via the interface.

In one or more exemplary methods of operating an accessory device, in accordance with a determination that the secondary criterion is satisfied, communicating the second indication indicative of the quality of the connection comprises displaying, on the display of the accessory device, a second user interface object representative of the second indication.

It is to be noted that descriptions of the accessory device being configured to perform acts also apply to the corresponding acts in the method of operating an accessory device and vice versa.

Also disclosed is a computer readable storage medium storing one or more programs, the one or more programs comprising instructions, which when executed by an accessory device with an interface, a memory and a processor cause the accessory device to perform any of the methods of operating an accessory device as described herein.

FIG. 1 illustrates an exemplary personal care system 1 embodied as an ostomy system 1A. The personal care system 1 (ostomy system 1A) comprises a personal care appliance 2 embodied as an ostomy appliance 2A including a base plate 4 and an ostomy pouch (not shown). Further, the personal care system 1 comprises a monitor device 6 and an accessory device 8 (mobile telephone, smartphone). The monitor device 6 is connectable to the personal care appliance 2, such as to base plate 4 and/or to an electrode assembly of or mounted to the personal care appliance, via respective first connectors of the monitor device 6 and base plate 4/electrode assembly. The monitor device 6 is configured for wireless communication via connection 9 with the accessory device 8. Optionally, the accessory device 8 is configured to communicate with a server device 10 of the personal care system 1, e.g. via network 12. The server device 10 may be operated and/or controlled by the ostomy appliance manufacturer and/or a service centre. Appliance data (ostomy data in the shown ostomy system) or parameter data based on the appliance data (ostomy data in the shown ostomy system) are obtained from electrodes/sensors of electrode assembly embedded in or mounted to the personal care appliance 2 with the monitor device 6. The monitor device 6 processes the appliance data and/or parameter data based on the appliance data to determine monitor data that are transmitted to the accessory device 8 via connection 9. In the illustrated personal care system, the accessory device 8 is a mobile phone, however the accessory device 8 may be embodied as another handheld device, such as a tablet device, or a wearable, such as a watch or other wrist-worn electronic device. Accordingly, the monitor device 6 is configured to determine monitor data and transmit the monitor data to the accessory device 8. The base plate 4 comprises a coupling member 14 in the form of a coupling ring 16 for coupling an ostomy pouch (not shown) to the base plate (two-part ostomy appliance). The base plate 4 has a stomal opening 18 with a center point 19. The size and/or shape of the stomal opening 18 is typically adjusted by the user or nurse before application of the ostomy appliance to accommodate the user's stoma.

The personal care system 1 optionally comprises a docking station 20 forming an accessory device of the personal care system 1. The docking station 20 comprises a docking monitor interface including a first connector 22 configured for electrically and/or mechanically connecting the monitor device 6 to the docking station 20. The docking monitor interface may be configured for wirelessly connecting the monitor device 6 to the docking station 20. The docking station 20 comprises a user interface 24 for receiving user input and/or providing feedback to the user on the operational state of the docking station 20. The user interface 24 may comprise a touch-screen. The user interface 24 may comprise one or more physical buttons and/or one or more visual indicators, such as light emitting diodes.

Figure 2:
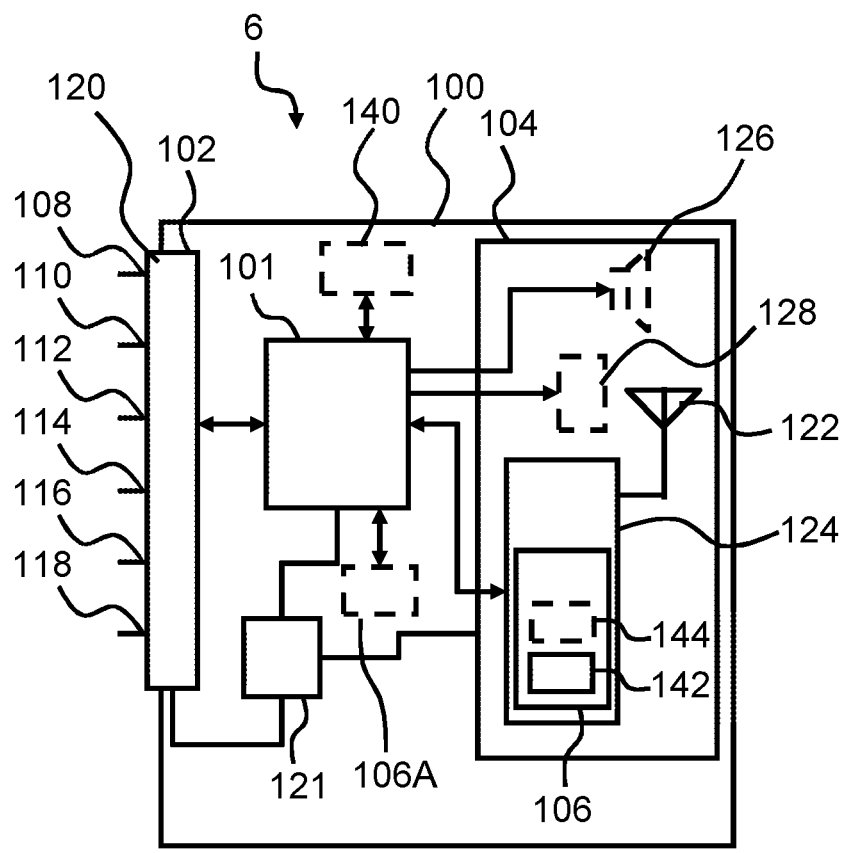
FIG. 2 illustrates an exemplary monitor device according to the present disclosure.

FIG. 2 is a schematic block diagram of an exemplary monitor device. The monitor device 6 comprises a monitor device housing 100, a processor 101, and one or more interfaces, the one or more interfaces including a first interface 102 (appliance interface) and a second interface 104 (accessory interface). The monitor device 6 comprises a memory 106/106A for storing monitor data based on appliance data and/or parameter data based on the monitor data. The memory 106/106A is optionally connected to the processor 101. The memory 106 is embedded optionally as flash memory in the second interface 104

The first interface 102 is configured as an appliance interface for electrically and/or mechanically connecting the monitor device 6 to the personal care appliance, e.g. ostomy appliance 2A or a wound dressing appliance. The first interface 102 comprises a plurality of terminals for forming electrical connections with respective terminals of the personal care appliance 2 (electrode assembly). The first interface 102 optionally comprises between four and 20 terminals, such as between six and twelve terminals, including a ground terminal 108, a first terminal 110, a second terminal 112 and a third terminal 114. The first interface 102 optionally comprises a fourth terminal 116 and a fifth terminal 118.

In one or more exemplary monitor devices, the first interface 102 optionally comprises a sixth terminal and/or a seventh terminal. The first interface 102 of the monitor device 6 comprises a coupling part 120 for forming a mechanical connection, such as a releasable coupling between the monitor device and the personal care appliance, e.g. with a base plate of an ostomy appliance and/or a electrode assembly of ostomy system/wound dressing system. The coupling part 120 and the terminals 108, 110, 112, 114, 116, and 118 of the first interface 102 form (at least part of) a first connector of the monitor device 6.

The monitor device 6 comprises a power unit 121 for powering the monitor device and active components thereof, i.e. the power unit 121 is connected to the processor 101, the first interface 102, and the second interface 104. The power unit comprises a battery and charging circuitry. The charging circuitry is connected to the battery and optionally to terminals of the first interface 102 for charging the battery via terminals of the first interface, e.g. terminals of the first connector. The charging circuitry may be configured for wireless charging of the battery.

The second interface 104 of monitor device is configured as an accessory interface for connecting the monitor device 6 to one or more accessory devices such as accessory device 8. The second interface 104 comprises an antenna 122 and a wireless transceiver 124 also denoted transceiver module, the wireless transceiver 124 connected to the processor 101 and configured for wireless communication with accessory device(s), such as configured for connecting the monitor device to the one or more accessory devices of the personal care system. Optionally, the second interface 104 comprises a loudspeaker 126 and/or a haptic feedback element 128 for provision of respective audio signal and/or haptic feedback to the user. The memory 106 may be an internal memory, such as flash memory of the wireless transceiver 124. Thereby, a separate memory module can be omitted which provides a simpler and lighter/smaller monitor device.

The monitor device 6 optionally comprises a sensor unit 140 connected to the processor 101. The sensor unit 140 may comprise a temperature sensor for feeding temperature data to the processor 101 and/or a G-sensor or accelerometer for feeding acceleration data to the processor 101.

The monitor device/processor 101/transceiver module 124 is configured to establish a connection between the monitor device and at least one of the one or more accessory devices, such as connection 9 to accessory device 8, determine whether a primary storing criterion based on a quality of the connection is satisfied; and in accordance with a determination that the primary storing criterion is satisfied, store primary monitor data 142 in the memory 106 according to a primary storing scheme SS_1.

The monitor device/processor 101/transceiver module 124 is configured to transmit monitor data to the accessory device, wherein to transmit monitor data to the accessory device optionally comprises to store monitor data in the memory according to a transmit storing scheme, e.g. use the memory as a buffer for transmission. The primary storing scheme is different from the transmit storing scheme. The primary storing scheme may have a primary storing frequency smaller than a transmit storing frequency of the transmit storing scheme and/or the primary storing scheme may have a first data size larger than a transmit data size of the transmit storing scheme.

The primary storing criterion SC_1 is optionally given as: SC_1: CP_1<TH_S_1, wherein CP_1 is a primary connection parameter being a received channel power indicator (RCPI) indicative of a quality of the connection and obtained from the transceiver module 124 and TH_S_1 is a primary storing threshold. In other words, the primary storing criterion based on a quality of the connection is satisfied when it is determined that the quality of the connection is below a threshold.

The monitor device/processor 101 is optionally configured to, in accordance with a determination that the primary storing criterion is satisfied, select or determine the primary storing scheme SS_1 from a plurality of storing schemes. In other words, the primary storing scheme may be selected from a set of storing schemes comprising a plurality of storing schemes. To select the primary storing scheme is optionally based on a first parameter indicative of time since a quality of the connection is less than a threshold (i.e. a time since the primary storing criterion was satisfied).

To select the primary storing scheme is optionally based on a second parameter indicative of available memory capacity of the memory.

To select the primary storing scheme is optionally based on an operating state of the personal care appliance and/or appliance data, such as one or more of first appliance sensor data, second appliance sensor data, third appliance sensor data, fourth appliance sensor data, fifth appliance sensor data, and sixth appliance sensor data obtained from respective sensors/electrode pairs of the personal care appliance via the first interface 102. To store primary monitor data 142 in the memory 106 according to a primary storing scheme SS_1 may comprise to store less monitor data than is transmitted during normal transmission.

The monitor device/processor 101 is optionally configured to store secondary monitor data 144 in the memory 106 according to a secondary storing scheme as described below.

The monitor device/processor 101 is optionally configured to determine whether a secondary storing criterion SC_2, e.g. based on an available memory capacity of the memory is satisfied; and in accordance with a determination that the secondary storing criterion is satisfied, store secondary monitor data 144 in the memory 106 according to a secondary storing scheme SS_2. To store secondary monitor data 144 in the memory 106 according to a secondary storing scheme SS_2 may comprise to store less monitor data and/or to store monitor data with reduced frequency and/or data size than is stored with the primary storing scheme.

The secondary storing criterion SC_2 being satisfied may indicate that the available memory capacity of the memory is low. In other words, the monitor device is optionally configured to dynamically adapt storing of the monitor data in the memory in turn resulting in improved utilisation of the memory resources in the monitor device. For example, the secondary storing criterion, also denoted SC_2, may be based on a secondary storage parameter, SP_2, associated with memory and being indicative of available memory capacity of the memory. The secondary storing criterion SC_2 may be given as: SC_2: SP_2<TH_M_2, wherein SP_2 is the secondary storage parameter and TH_M_2 is a secondary memory threshold.

In monitor device 6, to store secondary monitor data 144 optionally comprises compressing primary monitor data 142 or at least a part thereof in the memory. In other words, the monitor device 6 may be configured to free up memory in memory 106 by compressing the primary monitor data 144 stored during application of the primary storing scheme SS_1 and store the compressed primary monitor data in the memory. The compressed primary monitor data may be over-written on a part of the primary monitor data. In this way, primary monitor data of high importance may be kept in the memory, while less important primary monitor data may be deleted, In monitor device 6, to store secondary monitor data optionally comprises deleting, e.g. by over-writing, primary monitor data from the memory. To store secondary monitor data may comprise selecting a part of the primary monitor data, e.g. the oldest primary monitor data and/or primary monitor data of less importance/low priority, and overwriting the selected part of the primary monitor data with the secondary monitor data.

In monitor device 6, the monitor device is optionally configured to, in accordance with a determination that the secondary storing criterion is satisfied, select the secondary storing scheme from the plurality of storing schemes or determine the secondary storing scheme.

In monitor device 6, to select the secondary storing scheme is optionally based on a first parameter indicative of time since a quality of the connection is less than a threshold. In monitor device 6, to select the secondary storing scheme is optionally based on a first parameter indicative of time since a determination that the primary storing scheme was satisfied.

In monitor device 6, to select the secondary storing scheme is optionally based on a second parameter indicative of available memory capacity of the memory. In monitor device 6, to select the secondary storing scheme optionally comprises to select a first storing scheme as the secondary storing scheme if the second parameter indicative of available memory capacity is indicative of a large memory capacity, e.g. if the second parameter is larger than a first memory threshold, and/or to select a second storing scheme as the primary storing scheme if the second parameter indicative of available memory capacity is indicative of a small or reduced memory capacity, e.g. if the second parameter is less than a second memory threshold. The act to select the secondary storing scheme may be based on both the first parameter and the second parameter. In monitor device 6, to select the secondary storing scheme is optionally based on an operating state of the personal care appliance and/or appliance data, such as one or more of first appliance sensor data, second appliance sensor data, third appliance sensor data, fourth appliance sensor data, fifth appliance sensor data, and sixth appliance sensor data obtained from respective sensors/electrode pairs of the personal care appliance via the first interface 102.

The monitor device 6 is optionally configured to determine whether a transmission criterion TC based on the quality of the connection is satisfied; and in accordance with a determination that the transmission criterion is satisfied, transmit monitor data, including primary monitor data 142 and/or secondary monitor data 144, in the memory 106 to the accessory device. The transmission criterion being satisfied may indicate that the connection is resumed and/or returns to a satisfactory quality. In other words, the monitor device is optionally configured to transmit the monitor data in the memory stored during a time period of no or low-quality connection to the accessory device upon determination of reestablishment of the connection. For example, the transmission criterion, also denoted TC, may be based on a connection parameter, CP, associated with the connection and being indicative of a quality of the connection. The transmission criterion is optionally given as: TC: CP>TH_T, wherein CP is the connection parameter being a received channel power indicator (RCPI) from the transceiver module 124 and TH_T is a transmission threshold.

In monitor device 6, to transmit monitor data in the memory to the accessory device optionally comprises to transmit the secondary monitor data 144, and after transmitting the secondary monitor data 144, to transmit the primary monitor data 146. Thereby, the accessory device receiving the stored monitor data is able to determine and communicate a current operating state fast after resuming connection.

In one or more exemplary monitor devices, the primary monitor data comprises primary appliance data e.g. primary ostomy data obtained from an ostomy appliance being the personal care appliance via the first interface or primary wound dressing data obtained from a wound dressing being the personal care appliance via the first interface. In one or more exemplary monitor devices, the secondary monitor data comprises secondary appliance data, e.g. secondary ostomy data obtained from an ostomy appliance being the personal care appliance via the first interface or secondary wound dressing data obtained from a wound dressing being the personal care appliance via the first interface.

The processor 101 is configured to obtain appliance data based on appliance measurements via the terminals of the first interface 102. The processor 101 is configured to determine monitor data such as primary monitor data and/or secondary monitor data, based on the appliance data and optionally in accordance with a respective storing scheme.

Figure 3:
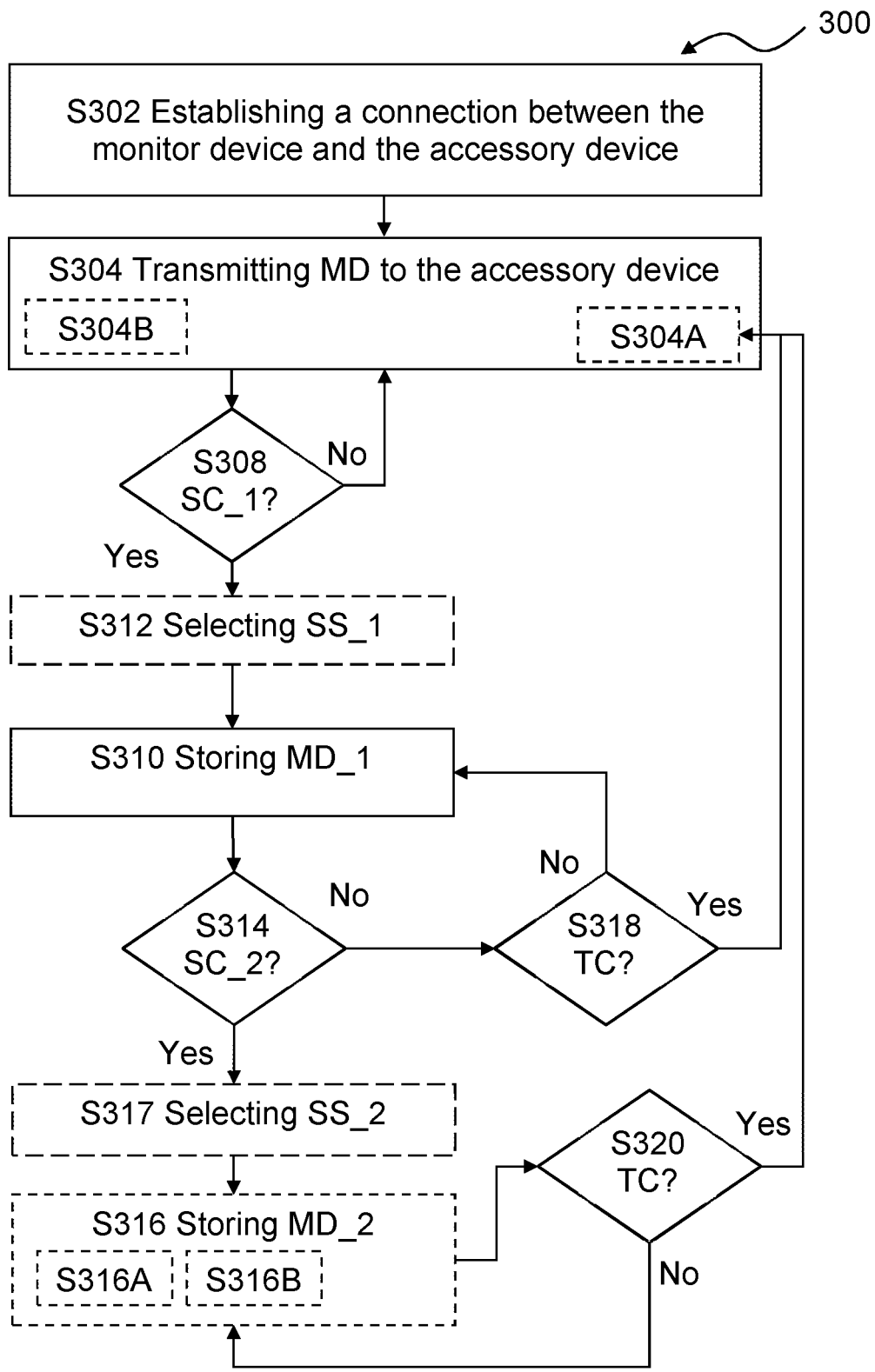
FIG. 3 is a flow diagram of an example method of operating a monitor device for a personal care system according to the present disclosure.

The processor 101 may be optionally configured to perform any of the operations disclosed in FIG. 3 (such as any one or more of S308, S310, S312, S314, S316, S316A, S316B, S317, S318, S320). The operations of the monitor device 100 may be embodied in the form of executable logic routines (such as, lines of code, software programs, etc.) that are stored on a non-transitory computer readable medium (such as, internal memory in the processor 101 or external memory) and are executed by the processor 101).

Furthermore, the operations of the monitor device 100 may be considered a method that the monitor device 100 is configured to carry out. Also, while the described functions and operations may be implemented in software, such functionality may as well be carried out via dedicated hardware or firmware, or some combination of hardware, firmware and/or software.

The memory 106 and/or 106A may be one or more of a buffer, a flash memory, a hard drive, a removable media, a volatile memory, a non-volatile memory, a random access memory (RAM), or other suitable device. In a typical arrangement, the memory 106 may include a non-volatile memory for long term data storage and a volatile memory that functions as system memory for the processor 106. The memory 106, 106A may exchange data with the processor 101 over a data bus. Control lines and an address bus between the memory 101 and the processor 402 also may be present (not shown in FIG. 2). The memory 106, 106A is considered a non-transitory computer readable medium.

FIG. 3 shows a flow diagram of an example method 300 of operating a monitor device for a personal care system, such as monitor device 6 of FIG. 2.

The method 300 comprises establishing S302 a connection between the monitor device and at least one of the one or more accessory devices; optionally transmitting S304 monitor data MD to the accessory device via the connection, determining S308 whether a primary storing criterion SC_1 based on a quality of the connection is satisfied; and in accordance with a determination that the primary storing criterion SC_1 is satisfied, storing S310 primary monitor data MD_1 in the memory according to a primary storing scheme SS_1.

In method 300, the act of determining S308 whether the primary storing criterion SC_1 based on a quality of the connection is satisfied optionally comprises determining whether the quality of the connection is below a threshold, e.g. wherein the primary storing criterion SC_1 may be given as: SC_1: CP_1<TH_S_1, wherein CP_1 is the primary connection parameter being a received channel power indicator (RCPI) and TH_S_1 is a primary storing threshold.

The method 300 optionally comprises, in accordance with a determination that the primary storing criterion SC_1 is satisfied, selecting S312 the primary storing scheme SS_1 from a plurality of storing schemes. Selecting S312 the primary storing scheme SS_1 is optionally based on one or more of a first parameter indicative of time since a quality of the connection is less than a threshold, a second parameter indicative of available memory capacity of the memory, and an operating state of the personal care appliance. The method 300 optionally comprises, in accordance with a determination that the primary storing criterion SC_1 is not satisfied proceed to transmitting S304 monitor data MD to the accessory device via the connection.

In method 300, transmitting S304 monitor data to the accessory device optionally comprises storing S304B monitor data in the memory according to a transmit storing scheme. The primary storing scheme SS_1 is different from and optionally requires less memory than the transmit storing scheme SS_T. The primary storing scheme SS_1 may have a primary storing frequency SF_1 smaller than a transmit storing frequency SF_T of the transmit storing scheme SS_T and/or the primary storing scheme SS_1 may have a first data size DS_1 smaller than a transmit data size DS_T of the transmit storing scheme SS_T.

The method 300 optionally comprises determining S314 whether a secondary storing criterion, e.g. based on an available memory capacity of the memory, is satisfied; and in accordance with a determination that the secondary storing criterion is satisfied, storing S316 secondary monitor data MD_2 in the memory according to a secondary storing scheme SS_2 different from the primary storing scheme SS_1. Storing S316 secondary monitor data MD_2 may comprise compressing S316A primary monitor data MD_1 in the memory optionally in accordance with a determination that the available memory capacity of the memory is less than a threshold, e.g. zero. Storing S316 secondary monitor data MD_2 may comprise deleting 316B primary monitor data MD_1 or at least a part thereof from the memory.

The method 300 optionally comprises, in accordance with a determination that the secondary storing criterion SC_2 is satisfied, selecting S317 the secondary storing scheme SS_2 from a plurality of storing schemes. Selecting S317 the secondary storing scheme SS_2 is optionally based on one or more of a first parameter indicative of time since a quality of the connection is less than a threshold, a second parameter indicative of available memory capacity of the memory, and an operating state of the personal care appliance The method 300 optionally comprises determining S318, e.g. in accordance with a determination that the secondary storing criterion is not satisfied, whether a transmission criterion TC based on the quality of the connection is satisfied; and in accordance with a determination that the transmission criterion is satisfied, transmitting S304A monitor data, such as primary monitor data and/or secondary monitor data, in the memory to the accessory device. The method 300 may in accordance with a determination that the transmission criterion is not satisfied in S318, proceed to storing S310 primary monitor data in the memory or selecting S312 the primary storing scheme. Transmitting S304A monitor data in the memory to the accessory device optionally comprises to transmit the secondary monitor data, and after transmitting the secondary monitor data, to transmit the primary monitor data.

The method 300 optionally comprises determining S320, e.g. after storing S316 secondary monitor data in the memory, whether a transmission criterion TC based on the quality of the connection is satisfied; and in accordance with a determination that the transmission criterion is satisfied, transmitting S304A monitor data, such as primary monitor data and/or secondary monitor data, in the memory to the accessory device. The method 300 may in accordance with a determination that the transmission criterion is not satisfied in S320, proceed to storing S316 secondary monitor data in the memory or selecting S317 the secondary storing scheme.

Figure 4:
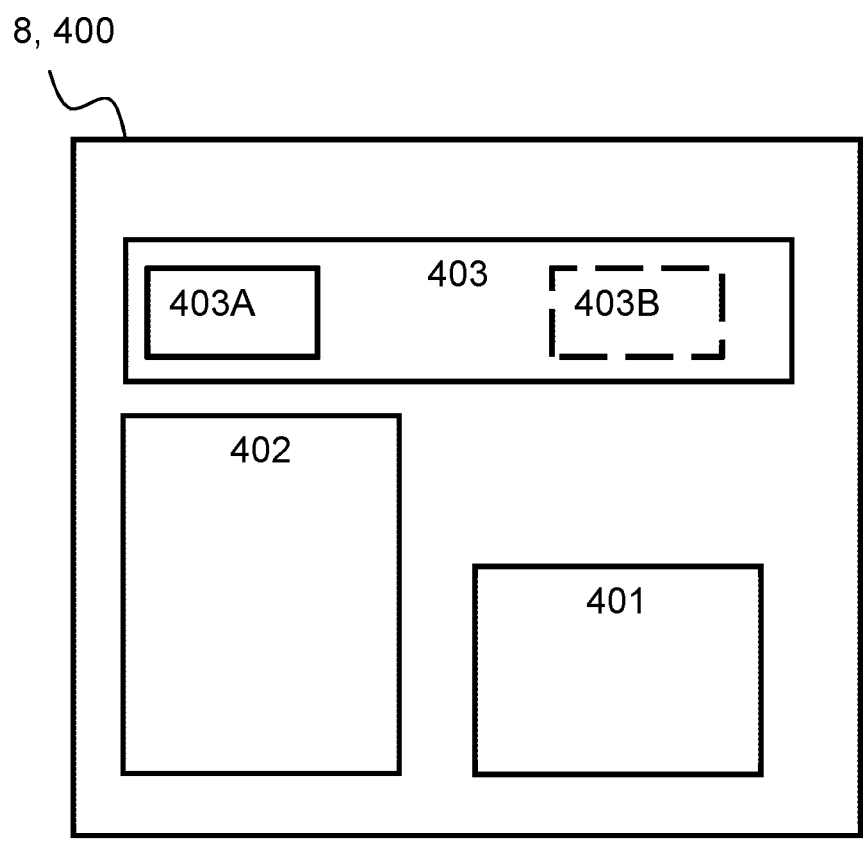
FIG. 4 is a block diagram illustrating an exemplary accessory device according to the present disclosure.

FIG. 4 is a block diagram illustrating an exemplary accessory device 400 according to the present disclosure. The accessory device 400 forms part of a personal care system, such as an ostomy system or a wound dressing system and is capable of supporting the monitoring of the operating state of an ostomy appliance or a wound dressing appliance to be placed on a user's skin. The accessory device 400 comprises a memory 401; a processor 402 coupled to the memory 401; and an interface 403, coupled to the processor 402.

Peripheral devices, such as memory 401 and/or interface 403 can be operatively and communicably coupled to the processor 402 via a bus for communicating data. The processor 402 can be a central processing unit (CPU), but other suitable microprocessors are also contemplated.

The interface 403 is configured to connect the accessory device to the monitor device of the personal care system, the interface comprising a transceiver module 403A connected to the processor 402.

The interface 403 may be configured to communicate with one or more devices of the personal care system. The one or more devices comprising a monitor device, and/or a personal care appliance configured to be placed on a skin surface of a user or on any additional seals. The interface 403 may comprise a display 403B as a visual interface to the user. The interface 403 is configured to establish a connection between the monitor device and the accessory device.

The interface 403 is configured to receive monitor data from the monitor device, such as to receive or retrieve the monitor data from the one or more devices. The monitor data may be indicative of a condition of the personal care appliance, such as a condition of a proximal side of a layer of the personal care appliance that is directed towards the skin surface or a condition of an absorbent core layer of the personal care appliance. In one or more exemplary accessory devices, the monitor data comprises appliance data, e.g. ostomy data or wound dressing data, obtained via the interface 403 from an ostomy appliance being the personal care appliance or from a wound dressing being the personal care appliance, respectively.

The processor 402 may be configured to determine an operating state of the personal care appliance based on the monitor data.

The processor 402 may be configured to determine whether a primary criterion based on a quality of the connection is satisfied. In one or more exemplary accessory devices, the primary criterion based on a quality of the connection is not satisfied when it is determined that the quality of the connection is not above a primary connection threshold. For example, the primary criterion based on a quality of the connection is not satisfied when it is determined that the quality of the connection is equal or below the primary connection threshold.

For example, the primary criterion, also denoted C_1, may be based on one or more connection parameters associated with the connection and being indicative of a quality of the connection, such as a signal strength indicator, e.g. a received signal strength indicator (RSSI) or a received channel power indicator (RCPI), signal-to-noise ratio, an error rate, e.g. a bit error rate, and/or a frame error rate, a number of non-acknowledgements (NACKs), and/or a number of retransmissions. In other words, the accessory device may be configured to determine whether the connection to the monitor device is lost by determining whether the primary criterion based on the quality of the connection is satisfied. Stated differently, the primary criterion based on a quality of the connection is not satisfied when it is determined that the quality of the connection is degraded (e.g. poor) and/or reduced, leading to a loss of connection to the monitor device. Thus, the accessory device is configured to communicate the first indication in case the connection to the monitor device is of low quality, e.g. lost or degraded.

The processor 402 may be configured to in accordance with a determination that the primary criterion is not satisfied, communicate, e.g. via the interface 403, a first indication indicative of the quality of the connection to the user. For example, the processor 402 may be configured to, in accordance with a determination that the primary criterion is not satisfied, communicate the first indication, e.g. to the user, e.g. via an output device (such as a display 403B and/or a loudspeaker). In one or more exemplary embodiments, the first indication may be communicated by sound. For example, the processor 402 is configured to, in accordance with a determination that the primary criterion is not satisfied, communicate, via the interface 403 (e.g. a transceiver module 403A), the first indication, e.g. to another device, e.g. an external device (such as wearable device, a smartphone, and/or a server device).

The personal care system comprises one or more of: an ostomy system, and a wound care system.

The accessory device 400 is capable of communicating a first indication indicative of a quality of the connection. The present disclosure improves the reliability of the monitoring performed by the personal care system, by communicating the first indication indicative of the quality of connection when a quality of the connection is not satisfactory. The accessory device 400 can notify appropriately the user and to start potentially estimating the operating state without real-time current monitor data. For example, communication of the first indication indicative of a quality of connection to the monitor device helps reducing the risk of a user experiencing a leakage (e.g. output leakage between a user's skin and the baseplate of the ostomy appliance) from an ostomy appliance in a planned activity and/or wet wound from a saturated wound dressing appliance. In particular, determination and communication the first indication indicative of an estimated operating state, and possibly with a latest operating state, according to the present disclosure is performed based on monitor data indicative of a condition of the ostomy appliance which may not be visible to the user.

In one or more exemplary accessory devices, the processor 402 is configured to, in accordance with a determination that the primary criterion is not satisfied, select, from a plurality of indications, the first indication indicative of the quality of the connection. In one or more exemplary accessory devices, the first indication is indicative of the operating state at a time where the primary criterion based on the quality of the connection is not satisfied. For example, the first indication is indicative of the operating state at a time where the connection is lost and/or degraded and/or interrupted. For example, the first indication may be selected from the plurality of indications comprising an indication indicative of the connection lost and/or degraded, and an indication is indicative of the operating state at a time where the primary criterion based on the quality of the connection is not satisfied.

In one or more exemplary accessory devices, to select the first indication indicative of the quality of the connection comprises to determine an estimated operating state of the personal care appliance based on one or more previous operating states of the personal care appliance. For example, the processor 402 determines the estimated operating state of the personal care appliance based on one or more previous operating states and selects the first indication amongst a plurality of indications including an indication indicative of the estimated operating state. The one or more previous operating states of the personal care appliance are determined by the accessory device before the time where the primary criterion based on the quality of the connection is not satisfied (e.g. before the time where the connection is lost). In one or more exemplary accessory devices, the first indication is indicative of the estimated operating state.

In one or more exemplary accessory devices, to determine the estimated operating state of the personal care appliance based on one or more previous operating states of the personal care appliance comprises to predict the estimated operating state of the personal care appliance based on the one or more previous operating states of the personal care appliance. For example, the processor 402 predicts the estimated operating state based on one or more previous operating states, such as based on one or more operating states previously determined by the accessory device (i.e. prior to loss of connection). The one or more operating states previously determined by the accessory device may relate the similar personal care appliances as the one currently used by the user. Optionally, one or more operating states previously determined by the accessory device may relate the different personal care appliances as the one currently used by the user, which have the characteristics and/or components which are the same as the one currently used by the user. Optionally, the processor 402 may be configured to determine the estimated operating state as a future operating state of the personal care appliance based on one or more previous operating states, such as based on one or more (future and/or current) operating states previously determined by the accessory device. In one or more exemplary accessory devices, the processor 402 may comprise a predictor. The predictor may be configured to predict operating state(s) based on a prediction function. It may be envisaged that the processor 402 may be configured to predict the estimated operating state of the personal care appliance by deriving a trend or a function of an operating state and/or the monitor data over the time period, e.g. for the similar personal care appliances as the one currently used by the user, or for similar base plates as the currently used one. The time period may include a time period up to and possibly including a current time. The time period may include a time period from a start time of use of any personal care appliances, to the current time of determination of the estimated operating state. The time period may include a time period from a start time of the loss of connection to the current time. The time period may include a time window that periodically occurs, such as a morning time period, an afternoon time period, a night time period, a daily time period, a weekly time period etc. The processor 402 may be configured to predict the estimated operating state based on a parameter characterizing a product type of the personal care appliance. The processor may be configured to predict (such as to determine) the estimated operating state based on monitor data obtained for similar product types of personal care appliances previously used by the user.

In one or more exemplary accessory devices, the processor 402 is configured to, in accordance with a determination that the primary criterion is not satisfied, communicate, e.g. via the interface 403, the first indication indicative of the quality of the connection, by displaying, on a display 403B, a first user interface object representative of the first indication. The first user interface object may be displayed as one or more media, such as text, graphic and/or video. The interface 403 may comprise the display 403B configured to display a user interface. The display 403B may comprise a touch sensitive surface. A user interface comprises one or more user interface objects. A user interface may be referred to as a user interface screen.

The display 403B may be configured to detect touch (e.g. the display is a touch-sensitive display), the input comprises a contact on the touch sensitive display. A touch-sensitive display provides an input interface and an output interface between the accessory device and a user. The processor 402 of the accessory device may be configured to receive and/or send electrical signals from/to touch-sensitive display. A touch-sensitive display is configured to display visual output to the user. The visual output optionally includes graphics, text, icons, video, and any combination thereof (collectively termed "graphics"). For example, some or all of the visual output may be seen as corresponding to user interface objects.

In one or more exemplary accessory devices, to communicate the first indication comprises to display, on a visual interface (e.g. a display 403B) of the accessory device, a user interface comprising a user interface object representative of the first indication, such as a first user interface object representative of the first indication indicative of the quality of the connection and/or representative of a first operating state of the personal care appliance, and/or representative of a second operating state of the personal care appliance. In one or more exemplary accessory devices, the user interface object representative of the first indication comprises a first user interface object representative of the first indication, and/or of one or more operating states.

In one or more exemplary accessory devices, to communicate the first indication comprises to notify the user via the interface, such as by displaying a notification on a display of the accessory device. The notification may comprise the first user interface object representative of the first indication. The notification may comprise a notification indicator to open an application related to the personal care appliance. The accessory device 400 may be configured to detect an input on the notification indicator. The accessory device 400 may be configured to, in response to the input, opening the application related to the ostomy appliance. The accessory device 400 may be configured to, in response to the opening of the application, to display a user interface object representative of an operating state (such as a latest operating state and/or an estimated operating state).

In one or more exemplary accessory devices, the processor 402 is configured to determine that a secondary criterion based on the quality of the connection is satisfied. For example, the secondary criterion based on a quality of the connection is satisfied when it is determined that the quality of the connection is above a secondary connection threshold. In one or more embodiments, the primary connection threshold is the same as the secondary connection threshold. In one or more embodiments, the primary connection threshold is different from the secondary connection threshold. It may be appreciated that having the primary connection threshold different from the secondary connection threshold may lead to a reduction of the hysteresis effect between the communication of the first indication and the communication of the second indication.

In one or more exemplary accessory devices, the processor 402 is configured to in accordance with a determination that the secondary criterion is satisfied, communicate (e.g. via the interface 403) a second indication indicative of the quality of the connection. In one or more exemplary accessory devices, the processor 402 is configured to in accordance with a determination that the secondary criterion is satisfied, determine the second indication. In one or more exemplary accessory devices, the second indication is indicative of the operating state at a time where the secondary criterion based on a quality of the connection is satisfied. For example, the first indication is indicative of the operating state at a time where the connection is lost and/or degraded and/or interrupted.

In one or more exemplary accessory devices, the processor 402 is configured to, in accordance with a determination that the secondary criterion is satisfied, resume (e.g. using the interface 403, such as using the transceiver 403A) reception of the monitor data from the monitor device. For example, the monitor data comprises one or more of: monitor data accumulated during a period of lost connection, e.g. primary monitor data and/or secondary monitor data, until resumption of connection, and real-time monitor data (e.g. "live" monitor data, e.g. monitor data received from resumption of connection).

In one or more exemplary accessory devices, the processor 402 is configured to, in accordance with a determination that the secondary criterion is satisfied, communicate the second indication indicative of the quality of the connection, by displaying, on the display of the accessory device, a second user interface object representative of the second indication. For example, the second user interface objection may convey: "something happened" or "everything is still good" (etc.) during the period of lost connection. For example, the processor 402 is configured to notify the user via the interface 403, such as by displaying a notification indicative of the second indication on the display 403B.

The memory 401 may be configured to store the monitor data and/or the operating state and/or the first indication(s) and/or second indication(s).

Figure 5A:
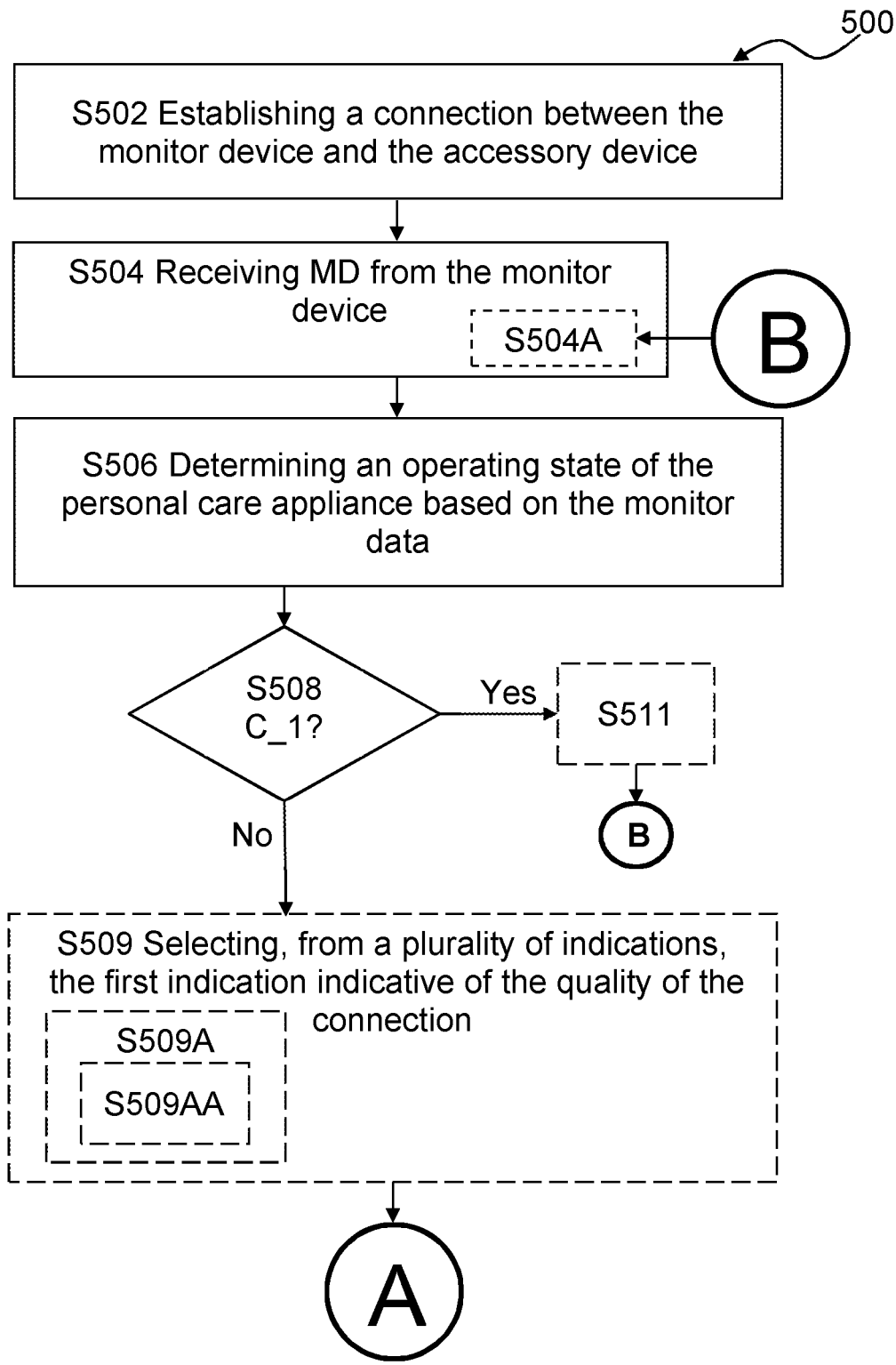
FIG. 5 is a flow diagram of an example method of operating an accessory device for a personal care system according to the present disclosure.
Figure 5B:
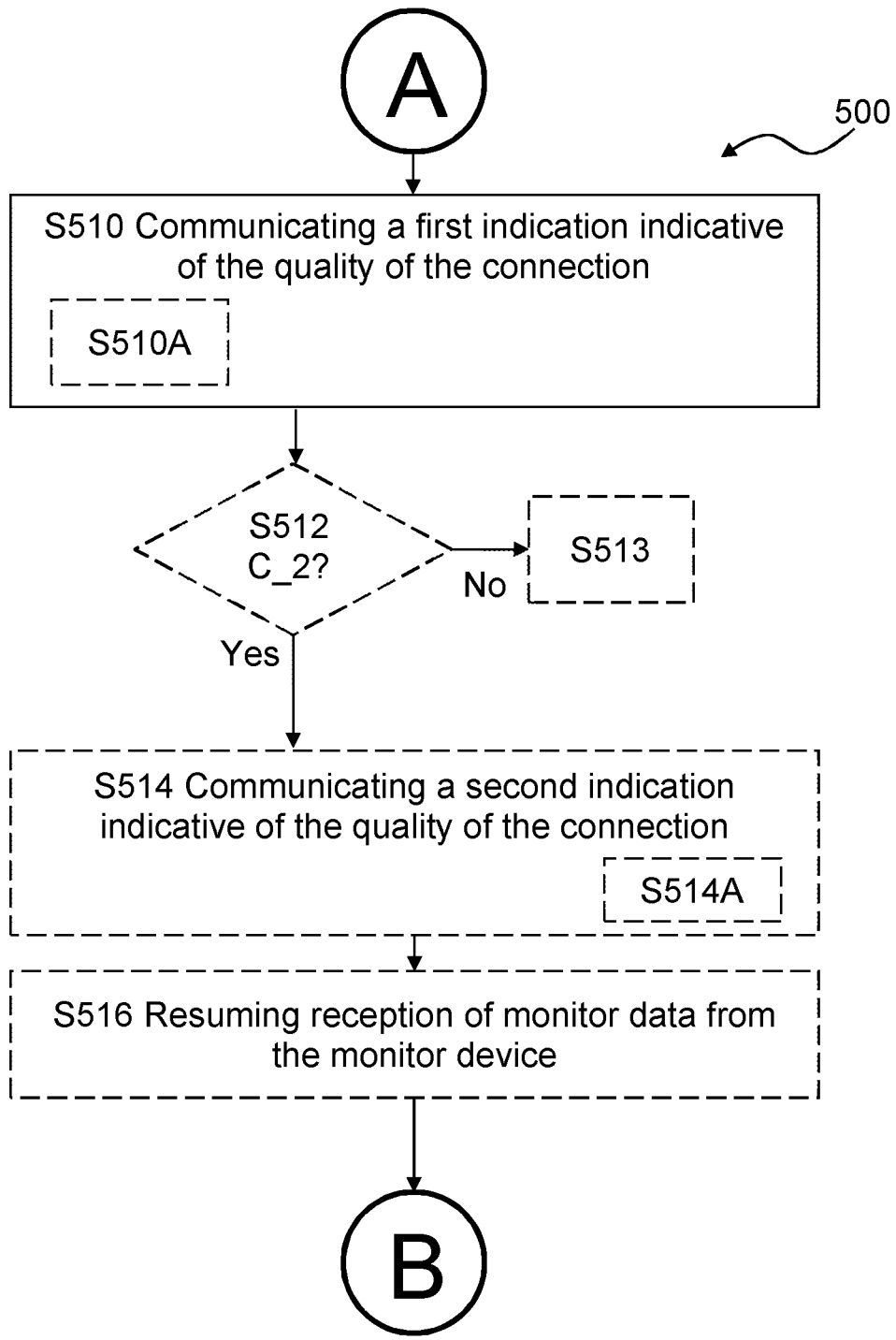

The processor 402 is optionally configured to perform any of the operations disclosed in FIGS. 5A and 5B.

The processor 402 may be optionally configured to perform any of the operations disclosed in FIG. 5 (such as any one or more of S509, S509A, A509AA, S511, S510A, S512, S513, S514, S516, S518, S518A). The operations of the accessory device 400 may be embodied in the form of executable logic routines (such as, lines of code, software programs, etc.) that are stored on a non-transitory computer readable medium (such as, the memory 401) and are executed by the processor 402).

Furthermore, the operations of the accessory device 400 may be considered a method that the accessory device 400 is configured to carry out. Also, while the described functions and operations may be implemented in software, such functionality may as well be carried out via dedicated hardware or firmware, or some combination of hardware, firmware and/or software.

The memory 401 may be one or more of a buffer, a flash memory, a hard drive, a removable media, a volatile memory, a non-volatile memory, a random access memory (RAM), or other suitable device. In a typical arrangement, the memory 401 may include a non-volatile memory for long term data storage and a volatile memory that functions as system memory for the processor 402. The memory 401 may exchange data with the processor 402 over a data bus. Control lines and an address bus between the memory 401 and the processor 402 also may be present (not shown in FIG. 4). The memory 401 is considered a non-transitory computer readable medium.

FIGS. 5A and 5B shows a flow diagram of an example method 500 of operating an accessory device for a personal care system. The personal care system comprises a personal care appliance, a monitor device, and the accessory device.

The method 500 comprises establishing S502 a connection between the monitor device and the accessory device. The method 500 comprises receiving S504 monitor data from the monitor device. The method 500 optionally comprises determining S506 an operating state of the personal care appliance based on the monitor data.

The method 500 comprises determining S508 whether a primary criterion C_1 based on a quality of the connection, such as based on a signal strength indicator e.g. a received signal strength indicator (RSSI) or a received channel power indicator (RCPI), is satisfied. Determining S506 an operating state of the personal care appliance based on the monitor data may be performed in accordance a determination that the primary criterion is satisfied.

The method 500 comprises, in accordance with a determination that the primary criterion is not satisfied, communicating S510 a first indication indicative of the quality of the connection.

The method 500 may comprise, in accordance with a determination that the primary criterion is satisfied, refraining S511 from communicating the first indication indicative of the quality of the connection.

In one or more exemplary methods, the primary criterion based on a quality of the connection is not satisfied when it is determined that the quality of the connection is not above a primary connection threshold. For example, the primary criterion based on a quality of the connection is not satisfied when it is determined that the quality of the connection is equal or below the primary connection threshold.

For example, the primary criterion, also denoted C_1, may be based on one or more connection parameters associated with the connection and being indicative of a quality of the connection, such as a signal strength indicator, e.g. a received signal strength indicator (RSSI) or a received channel power indicator (RCPI), signal-to-noise ratio, an error rate, e.g. a bit error rate, and/or a frame error rate, a number of non-acknowledgements (NACKs), and/or a number of retransmissions. In other words, the accessory device may be configured to determine whether the connection to the monitor device is lost by determining whether the primary criterion based on the quality of the connection is satisfied. Stated differently, the primary criterion based on a quality of the connection is not satisfied when it is determined that the quality of the connection is degraded (e.g. poor) and/or reduced, leading to a loss of connection to the monitor device. Thus, the accessory device is configured to communicate the first indication in case the connection to the monitor device is of low quality, e.g. lost or degraded.

In one or more exemplary methods, the method 500 comprises, in accordance with a determination that the primary criterion is not satisfied, selecting S509, from a plurality of indications, the first indication indicative of the quality of the connection. For example, the first indication may be selected from the plurality of indications comprising an indication indicative of the connection lost and/or degraded, and an indication is indicative of the operating state at a time where the primary criterion based on the quality of the connection is not satisfied.

In one or more exemplary methods, the method 500 comprises communicating S510 the first indication indicative of the quality of the connection in accordance with a determination that the primary criterion is not satisfied comprises displaying S510A, on a display of the accessory device, a first user interface object representative of the first indication.

In one or more exemplary methods, selecting S509 the first indication indicative of the quality of the connection comprises determining S509A an estimated operating state of the personal care appliance based on one or more previous operating states of the personal care appliance.

In one or more exemplary methods, determining S509A the estimated operating state of the personal care appliance based on the one or more previous operating states of the personal care appliance comprises predicting S509AA the estimated operating state of the personal care appliance based on the one or more previous operating states of the personal care appliance.

In one or more exemplary methods, the first indication is indicative of the estimated operating state.

In one or more exemplary methods, the first indication is indicative of the operating state at a time where the primary criterion based on a quality of the connection is not satisfied.

In one or more exemplary methods, the first indication is indicative of the estimated operating state.

In one or more exemplary methods, the first indication is indicative of a time since the primary criterion based on a quality of the connection was not satisfied and/or a time where the primary criterion based on a quality of the connection was not satisfied.

In one or more exemplary methods, the method comprises determining S512 whether a secondary criterion C_2 based on the quality of the connection is satisfied. The secondary criterion being satisfied may indicate that the connection is resumed and/or returns to a satisfactory quality. For example, the secondary criterion, also denoted C_2, may be based on a connection parameter, CP, associated with the connection and being indicative of a quality of the connection. The secondary criterion C_2 may be given as: C_2: CP>TH_C_2, wherein CP is the connection parameter being a signal strength indicator, such as a received signal strength indicator (RSSI) or a received channel power indicator (RCPI), and TH_C_2 is a secondary connection threshold.

In one or more exemplary methods, the method comprises, in accordance with a determination that the secondary criterion is satisfied, communicating S514 a second indication indicative of the quality of the connection.

The method 500 may comprise, in accordance with a determination that the primary criterion is satisfied, refraining S513 from communicating the second indication indicative of the quality of the connection.

In one or more exemplary methods, the second indication is indicative of the operating state at a time where the secondary criterion based on the quality of the connection is satisfied.

In one or more exemplary methods, the method comprises resuming reception S516 of the monitor data from the monitor device in accordance with a determination that the secondary criterion is satisfied.

In one or more exemplary methods, after resuming the reception of monitor data, the method proceeds to S504A receiving primary monitor data and/or secondary monitor data from the monitor device.

In one or more exemplary methods, in accordance with a determination that the secondary criterion is satisfied, communicating S514 the second indication indicative of the quality of the connection comprises displaying S514A, on the display of the accessory device, a second user interface object representative of the second indication.

Figure 6:
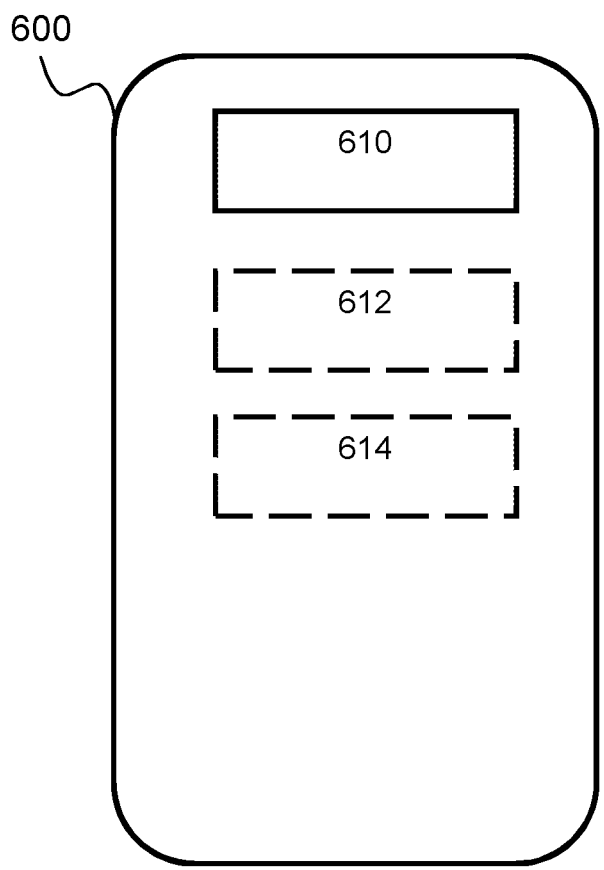
FIG. 6 shows one or more exemplary user interfaces for communicating the first indication according to the present disclosure.

FIG. 6 illustrates one or more exemplary user interfaces for communicating the first indication according to the present disclosure. FIG. 6 shows an exemplary user interface 600 for communicating the first indication via a visual interface of the accessory device, such as a display of the accessory device.

The user interface 600 comprises a first user interface object 610 representative of the first indication indicative of the quality of connection between the monitor device and the accessory device. The first user interface object 610 may be displayed as one or more media, such as text, graphic and/or video.

The first user interface object 610 may be user-interactive, or selectable by a user input. For example, an image (e.g., icon), a button, and text (e.g., hyperlink) each optionally constitute the first user interface object 610. The first user interface object 610 may form part of a widget.

The user interface 600 may comprise one or more, such as a plurality of user interface objects. For example, the user interface may comprise a first primary user interface object 612 representative of the first indication indicative of an operating state at the time of connection loss. For example, the user interface may comprise a first secondary user interface object 614 representative of the first indication indicative of an estimated operating state The accessory device is optionally configured to change dynamically the visual appearance of any of the user interface objects 610, 612, 614 based on the operating state. e.g. in terms of text, colour, shape, form, contrast, brightness, animation and/or blurring to indicate the operating state (latest or estimated for current time). For example, the severity of the operating state may be displayed, by the accessory device, by varying in colour: e.g. blue, yellow, red for indicating low, medium, high severity respectively. For example, the severity of the operating state may be displayed, by the accessory device, by varying shades within a colour from a lighter shade to a darker shade for indicating low to high severity respectively. For example, the severity of the operating state may be displayed, by the accessory device, by varying a magnitude of the visual effect (e.g., less blurring, sharper contrast) as severity increases.

For example, the user interface object 610 and/or 612, and/or 614 may be representative of an operating state indicating to change NOW the personal care by adopting e.g. the colour red, in a dark shade, in sharp contrast.

In one or more exemplary user interfaces, the user interface 600 comprises user interface objects 610, 612, 614 which separately or together, display a text prompt indicating to the user the first indication. A text prompt may for example indicate: "Monitor connection lost—Everything is fine", "Monitor connection lost—Good", "Monitor connection lost—Check", "Monitor connection lost—Change".

For example, the user interface object 610 and/or 612, and/or 614 may be displayed as one or more notifications, such as in a notification centre displayed on the display.

The accessory device may be configured to provide the user interface 600 in a user application running on the processor. The user application may be a dedicated personal care application that assist the user in monitoring the internal operating state of the personal care appliance.

The accessory device may be configured to provide the user interface 600 on a lock screen displayed by the accessory device.

The accessory device may be configured to provide the user interface 600 on a home screen displayed by the accessory device.

Figure 7:
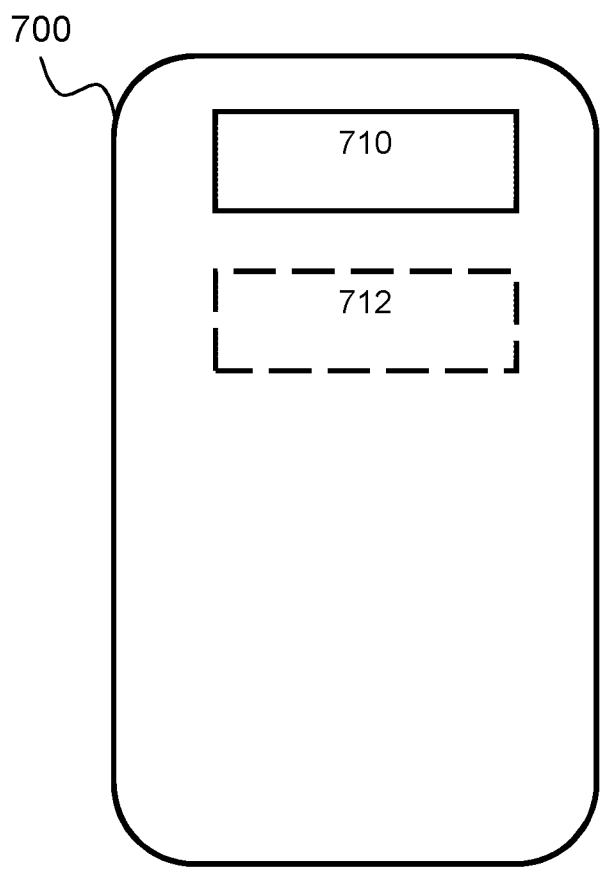
FIG. 7 shows one or more exemplary user interfaces for communicating the second indication according to the present disclosure.

FIG. 7 shows an exemplary user interface 700 for communicating the second indication via a visual interface of the accessory device, such as a display of the accessory device.

The user interface 700 comprises a second user interface object 710 representative of the second indication indicative of the quality of connection between the monitor device and the accessory device. The second user interface object 710 may be displayed as one or more media, such as text, graphic and/or video.

The second user interface object 710 may be user-interactive, or selectable by a user input. For example, an image (e.g., icon), a button, and text (e.g., hyperlink) each optionally constitute the second user interface object 710. The second user interface object 710 may form part of a widget.

The user interface 700 may comprise one or more, such as a plurality of user interface objects. For example, the user interface may comprise a second primary user interface object 712 representative of the second indication indicative of an operating state at the time of connection resumed (at a time where the secondary criterion based on a quality of the connection is satisfied).

The accessory device is configured to change dynamically the visual appearance of any of the user interface object 712 based on the operating state. e.g. in terms of colour, shape, form, contrast, brightness, animation and/or blurring to indicate the operating state (latest or estimated for current time). For example, the severity of the operating state may be displayed, by the accessory device, by varying in colour: e.g. blue, yellow, red for indicating low, medium, high severity respectively. For example, the severity of the operating state may be displayed, by the accessory device, by varying shades within a colour from a lighter shade to a darker shade for indicating low to high severity respectively. For example, the severity of the operating state may be displayed, by the accessory device, by varying a magnitude of the visual effect (e.g., less blurring, sharper contrast) as severity increases.

For example, the user interface object 710 and/or 712, may be representative of an operating state indicating to change NOW the personal care by adopting e.g. the colour red, in a dark shade, in sharp contrast.

In one or more exemplary user interfaces, the user interface 700 comprises user interface objects 710, 712 which separately or together, display a text prompt indicating to the user the second indication. A text prompt may for example indicate: "Monitor connection resumed—Everything is fine", "Monitor connection resumed—Good", "Monitor connection resumed—Check", "Monitor connection resumed—Change".

For example, the user interface object 710 and/or 712, may be displayed as one or more notifications, such as in a notification centre displayed on the display.

The accessory device may be configured to provide the user interface 700 in the user application running on the processor dedicated to personal care.

The accessory device may be configured to provide the user interface 700 on a lock screen displayed by the accessory device.

Figure 8:
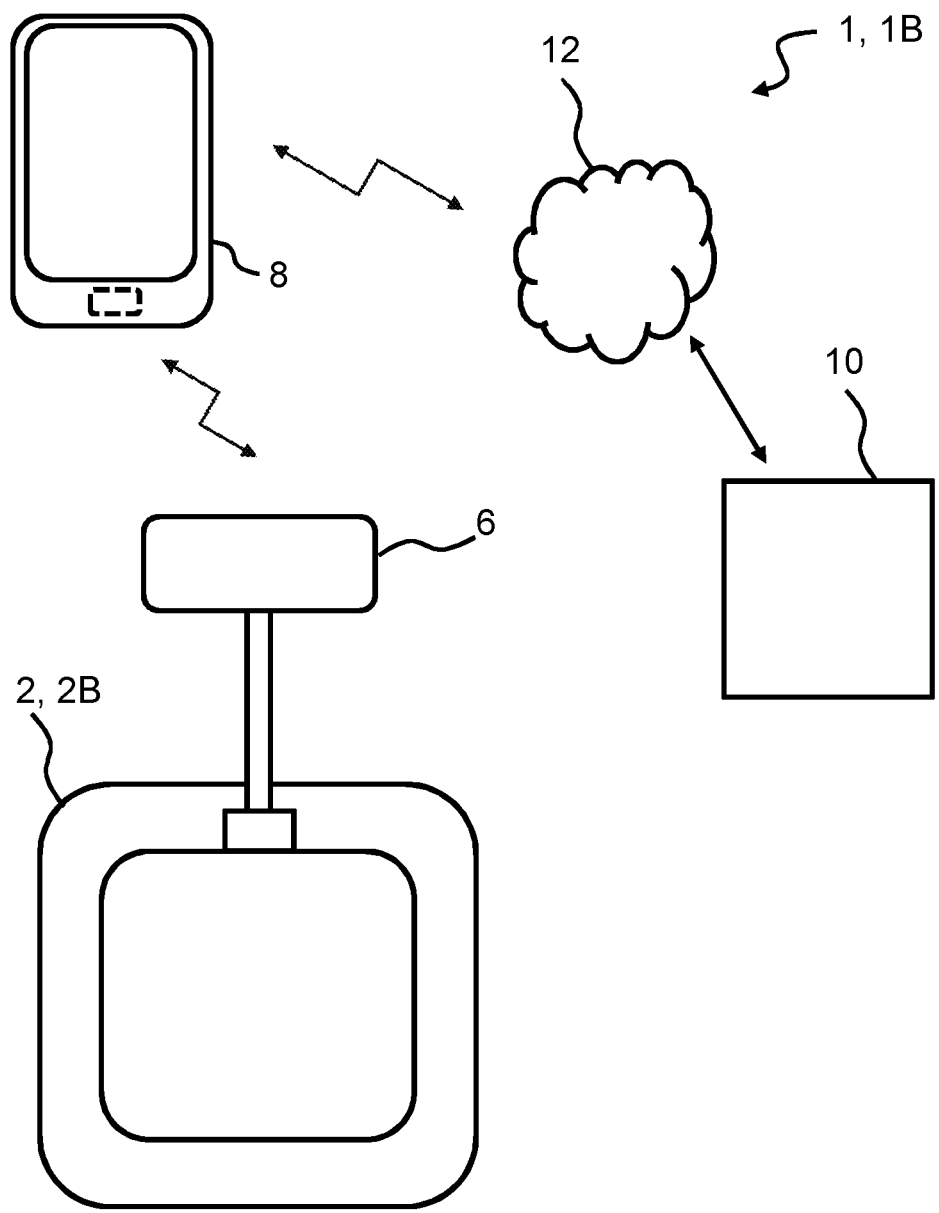
FIG. 8 illustrates an exemplary personal care system being a wound dressing system.

FIG. 8 illustrates an exemplary personal care system 1 embodied as a wound dressing system 1B. The personal care system 1 (wound dressing system 1B) comprises a personal care appliance 2 embodied as a wound dressing 2B. Further, the personal care system 1 comprises a monitor device 6 and an accessory device 8 (mobile telephone, smartphone). The monitor device 6 is connectable to the personal care appliance 2, such as to wound dressing 2B and/or to an electrode assembly of or mounted to the wound dressing, via respective first connectors of the monitor device 6 and wound dressing 2B/electrode assembly.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Furthermore, the labelling of a first element does not imply the presence of a second element and vice versa.

It may be appreciated that FIGS. 1-8 comprise some modules or operations which are illustrated with a solid line and some modules or operations which are illustrated with a dashed line. The modules or operations which are comprised in a solid line are modules or operations which are comprised in the broadest example embodiment. The modules or operations which are comprised in a dashed line are example embodiments which may be comprised in, or a part of, or are further modules or operations which may be taken in addition to the modules or operations of the solid line example embodiments. It should be appreciated that these operations need not be performed in order presented. Furthermore, it should be appreciated that not all of the operations need to be performed. The exemplary operations may be performed in any order and in any combination.

It is to be noted that the word "comprising" does not necessarily exclude the presence of other elements or steps than those listed.

It is to be noted that the words "a" or "an" preceding an element do not exclude the presence of a plurality of such elements.

It should further be noted that any reference signs do not limit the scope of the claims, that the exemplary embodiments may be implemented at least in part by means of both hardware and software, and that several "means", "units" or "devices" may be represented by the same item of hardware.

The various exemplary methods, devices, and systems described herein are described in the general context of method steps processes, which may be implemented in one aspect by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Generally, program modules may include routines, programs, objects, components, data structures, etc. that perform specified tasks or implement specific abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES 1 personal care system
1A ostomy system
1B wound dressing system
2 personal care appliance
2A ostomy appliance
2B wound dressing appliance
4 base plate
6 monitor device
8 accessory device
9 connection
10 server device
12 network
14 coupling member
16 coupling ring
18 stoma-receiving opening
19 center of the opening
20 docking station
22 first connector
24 user interface
100 monitor device housing
101 processor
102 first interface
104 second interface
106, 106A memory
108 ground terminal of monitor device
110 first terminal of monitor device
112 second terminal of monitor device
114 third terminal of monitor device
116 fourth terminal of monitor device
118 fifth terminal of monitor device
120 coupling part
121 power unit
122 antenna
124 wireless transceiver, transceiver module
126 loudspeaker
128 haptic feedback element
140 sensor unit
142, MD_1 primary monitor data
144, MD_2 secondary monitor data
300 method of operating a monitor device for a personal care system
S302 establishing a connection between the monitor device and at least one of the one or more accessory devices
S304 transmitting monitor data to the accessory device via the connection
S304A transmitting monitor data, such as primary monitor data and/or secondary monitor data, in the memory to the accessory device
S304B storing monitor data in the memory according to a transmit storing scheme
S308 determining whether a primary storing criterion based on a quality of the connection is satisfied
S310 storing primary monitor data in the memory according to a primary storing scheme
S312 selecting the primary storing scheme from a plurality of storing schemes
S314 determining whether a secondary storing criterion is satisfied
S316 storing secondary monitor data in the memory according to a secondary storing scheme
S316A compressing primary monitor data in the memory.
S316B deleting primary monitor data or at least a part thereof from the memory
S317 selecting the secondary storing scheme from a plurality of storing schemes
S318 determining whether a transmission criterion based on the quality of the connection is satisfied
400 accessory device
401 memory of accessory device
402 processor of accessory device
403 interface of accessory device
403 transceiver
403B display
500 Method of operating an accessory device
S502 establishing a connection between the monitor device and the accessory device.
S504 receiving monitor data from the monitor device
S504A receiving primary monitor data and/or secondary monitor data from the monitor device
S506 determining an operating state of the personal care appliance based on the monitor data.
S508 determining whether a primary criterion based on a quality of the connection is satisfied.
S509 selecting, from a plurality of indications, the first indication indicative of the quality of the connection
S509A determining the estimated operating state of the personal care appliance based on the one or more previous operating states of the personal care appliance S509AA predicting the estimated operating state of the personal care appliance based on the one or more previous operating states of the personal care appliance
S510 communicating a first indication indicative of the quality of the connection
S511 refraining from communicating the first indication indicative of the quality of the connection
S512 determining whether a secondary criterion based on the quality of the connection is satisfied
S513 refraining from communicating the second indication indicative of the quality of the connection
S514 communicating a second indication indicative of the quality of the connection
S514A displaying, on the display of the accessory device, a second user interface object representative of the second indication
S516 resuming reception of monitor data from the monitor device in accordance with a determination that the secondary criterion is satisfied
600 user interface
610 first user interface object
612 first primary user interface object
614 first secondary user interface object
700 user interface
710 second user interface object
712 second primary user interface object

The invention claimed is:

1. A personal care system comprising:
a personal care appliance,
one or more accessory devices, and
a monitor device, the monitor device comprising:
  a processor;
  a memory connected to the processor;
  a first interface connected to the processor, the first interface configured for connecting the monitor device to the personal care appliance; and
  a second interface comprising a transceiver module connected to the processor and configured for connecting the monitor device to the one or more accessory devices of the personal care system,
  wherein the monitor device is configured to:
    establish a connection between the monitor device and at least one of the one or more accessory devices;
    determine whether a primary storing criterion based on a quality of the connection is satisfied; and
    in accordance with a determination that the primary storing criterion is satisfied:
      select a primary storing scheme from a plurality of storing schemes; and
      store primary monitor data in the memory according to the primary storing scheme.

2. The personal care system according to claim 1, wherein the primary storing criterion based on a quality of the connection is satisfied when it is determined that the quality of the connection is below a threshold.

3. The personal care system according to claim 1, wherein to select the primary storing scheme is based on at least one of:
a first parameter indicative of time since a quality of the connection is less than a threshold;
a second parameter indicative of available memory capacity of the memory; and
an operating state of the personal care appliance.

4. The personal care system according to claim 1, wherein the monitor device is configured to:
determine whether a secondary storing criterion based on an available memory capacity of the memory is satisfied; and
in accordance with a determination that the secondary storing criterion is satisfied, store secondary monitor data in the memory according to a secondary storing scheme of the plurality of storing schemes.

5. The personal care system according to claim 4, wherein the storing of secondary monitor data comprises at least one of:
compressing primary monitor data in the memory; and
deleting primary monitor data from the memory.

6. The personal care system according to claim 1, wherein the monitor device is configured to:
determine whether a transmission criterion based on the quality of the connection is satisfied; and
in accordance with a determination that the transmission criterion is satisfied, transmit monitor data in the memory to the accessory device.

7. The personal care system according to claim 6, wherein the monitor device is configured to:
determine whether a secondary storing criterion based on an available memory capacity of the memory is satisfied; and
in accordance with a determination that the secondary storing criterion is satisfied, store secondary monitor data in the memory according to a secondary storing scheme of the plurality of storing schemes, and
wherein the transmitting of monitor data in the memory to the accessory device comprises transmitting the secondary monitor data, and after transmitting the secondary monitor data, transmitting the primary monitor data.

8. The personal care system according to claim 1, wherein the memory is a flash memory of the transceiver module, and wherein storing primary monitor data in the memory according to the primary storing scheme is based on one or more control parameters from the processor to the transceiver module.

9. The personal care system according to claim 1, wherein the primary monitor data comprises:
primary ostomy data obtained from an ostomy appliance being the personal care appliance via the first interface; or
primary wound dressing data obtained from a wound dressing being the personal care appliance via the first interface.

10. A method of operating a monitor device for a personal care system comprising a personal care appliance, the monitor device, and one or more accessory devices, the method comprising:
establishing a connection between the monitor device and at least one of the one or more accessory devices;
determining whether a primary storing criterion based on a quality of the connection is satisfied; and
in accordance with a determination that the primary storing criterion is satisfied;
selecting a primary storing scheme from a plurality of storing schemes; and
storing primary monitor data in a memory of the monitor device according to the primary storing scheme.

11. The method according to claim 10, wherein determining whether the primary storing criterion based on a quality of the connection is satisfied comprises determining whether the quality of the connection is below a threshold.

12. The method according to claim 10, wherein selecting the primary storing scheme is based on at least one of:
- a first parameter indicative of time since a quality of the connection is less than a threshold;
- a second parameter indicative of available memory capacity of the memory; and
- an operating state of the personal care appliance.

13. The method according to claim 10, the method comprising:
- determining whether a secondary storing criterion based on an available memory capacity of the memory is satisfied; and
- in accordance with a determination that the secondary storing criterion is satisfied, storing secondary monitor data in the memory according to a secondary storing scheme of the plurality of storing schemes.

14. The method according to claim 13, wherein storing secondary monitor data comprises at least one of:
- compressing primary monitor data in the memory; and
- deleting primary monitor data from the memory.

15. The method according to claim 10, the method comprising:
- determining whether a transmission criterion based on the quality of the connection is satisfied; and
- in accordance with a determination that the transmission criterion is satisfied, transmitting monitor data in the memory to the accessory device.

16. The method according to claim 15, the method comprising:
- determining whether a secondary storing criterion based on an available memory capacity of the memory is satisfied; and
- in accordance with a determination that the secondary storing criterion is satisfied, storing secondary monitor data in the memory according to a secondary storing scheme of the plurality of storing schemes, and
- wherein transmitting monitor data in the memory to the accessory device comprises transmitting the secondary monitor data, and after transmitting the secondary monitor data, transmitting the primary monitor data.

17. The method according to claim 10, wherein the memory is a flash memory of the transceiver module, and wherein storing primary monitor data in the memory according to the primary storing scheme is based on one or more control parameters from the processor to the transceiver module.

18. The method according to claim 10, wherein the personal care appliance is an ostomy appliance, and the method comprising obtaining primary ostomy data from the ostomy appliance and including the primary ostomy data in the primary monitor data; or wherein the personal care appliance is a wound dressing, and the method comprising obtaining primary wound dressing data from the wound dressing and including the primary wound dressing data in the primary monitor data.

19. A system, comprising:
- at least one processor; and
- memory storing instructions that, when executed by the at least one processor, cause the system to perform a set of operations, the set of operations comprising:
  - establishing a connection between the monitor device and at least one of the one or more accessory devices;
  - determining whether a primary storing criterion based on a quality of the connection is satisfied; and
  - in accordance with a determination that the primary storing criterion is satisfied;
  - selecting a primary storing scheme from a plurality of storing schemes; and
  - storing primary monitor data in a memory of the monitor device according to the primary storing scheme.

20. The system of claim 19, wherein the set of operations further comprises:
- determining whether a secondary storing criterion based on an available memory capacity of the memory is satisfied; and
- in accordance with a determination that the secondary storing criterion is satisfied;
- selecting a second primary storing scheme from the plurality of storing schemes; and
- storing secondary monitor data in the memory according to the secondary storing scheme.

* * * * *